(12) United States Patent  
Breeland et al.

(10) Patent No.: US 11,798,046 B2
(45) Date of Patent: Oct. 24, 2023

(54) HEALTH-CARE SYSTEMS AND METHODS

(71) Applicant: ALIGN TECHNOLOGY, INC., San Jose, CA (US)

(72) Inventors: Joe Breeland, Austin, TX (US); Amir Abolfathi, Menlo Park, CA (US); David Etheridge, El Granada, CA (US); Jason Shelton, El Granada, CA (US)

(73) Assignee: Align Technology, Inc., San Jose, CA (US)

( * ) Notice: Subject to any disclaimer, the term of this patent is extended or adjusted under 35 U.S.C. 154(b) by 267 days.

(21) Appl. No.: 16/825,933

(22) Filed: Mar. 20, 2020

(65) Prior Publication Data

US 2020/0234354 A1 Jul. 23, 2020

Related U.S. Application Data

(63) Continuation of application No. 11/033,097, filed on Jan. 11, 2005, now abandoned.

(51) Int. Cl.
*G05B 19/4099* (2006.01)
*G06Q 30/06* (2023.01)
*G16H 10/60* (2018.01)

(52) U.S. Cl.
CPC .......... *G06Q 30/06* (2013.01); *G16H 10/60* (2018.01)

(58) Field of Classification Search
CPC ....... A61C 7/00; A61C 9/0046; A61C 9/0053; A61C 13/0004; G05B 19/4099
USPC ........................................................ 433/213
See application file for complete search history.

(56) References Cited

U.S. PATENT DOCUMENTS

| 2,467,432 | A | 4/1949 | Kesling |
| 3,407,500 | A | 10/1968 | Kesling |
| 3,600,808 | A | 8/1971 | Reeve et al. |
| 3,660,900 | A | 5/1972 | Andrews et al. |
| 3,683,502 | A | 8/1972 | Wallshein et al. |
| 3,738,005 | A | 6/1973 | Cohen et al. |
| 3,860,803 | A | 1/1975 | Levine |
| 3,916,526 | A | 11/1975 | Schudy |
| 3,922,786 | A | 12/1975 | Lavin |

(Continued)

FOREIGN PATENT DOCUMENTS

| AU | 3031677 A | 5/1979 |
| AU | 517102 B2 | 7/1981 |

(Continued)

OTHER PUBLICATIONS

Web-based 3D Online Crown Preparation Course for Dental Students, Heiko Spallek, DMD, PhD, Ronald Kaise, Kenneth Boberick, DMD; Daniel Boston, DMD, Titus Schleyer, DMD, PhD, 2000 AMIA, Inc (Year: 2000).*

(Continued)

*Primary Examiner* — Dilek B Cobanoglu
(74) *Attorney, Agent, or Firm* — Wilson Sonsini Goodrich & Rosati

(57) ABSTRACT

A virtual health-care electronic commerce community includes a network to communicate information relating to the community; one or more patients coupled to the network; one or more treating professionals coupled to the network; and a server coupled to the network, the server storing data for each patient and performing patient data visualization in response to a user request.

20 Claims, 22 Drawing Sheets

(56) References Cited

U.S. PATENT DOCUMENTS

| | | |
|---|---|---|
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,005,126 A | 4/1991 | Haskin |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,053,883 A | 10/1991 | Johnson |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A * | 10/1993 | Riley ............... G05B 19/4099 |
| | | 700/182 |
| 5,273,429 A | 12/1993 | Rekow et al. |
| 5,278,756 A | 1/1994 | Lemchen et al. |
| 5,328,362 A | 7/1994 | Watson et al. |
| 5,338,198 A * | 8/1994 | Wu ................... A61C 9/0053 |
| | | 433/213 |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,590,248 A | 12/1996 | Zarge et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A * | 10/1998 | Schmitt ............. A61C 13/0004 |
| | | 433/214 |
| 5,848,115 A | 12/1998 | Little et al. |
| 5,851,115 A | 12/1998 | Carlsson et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,882,192 A | 3/1999 | Bergersen |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 5,995,138 A * | 11/1999 | Beer .................. H04N 1/00567 |
| | | 396/16 |
| 6,015,289 A | 1/2000 | Andreiko et al. |
| 6,044,170 A | 3/2000 | Migdal et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,089,868 A | 7/2000 | Jordan et al. |
| 6,091,982 A | 7/2000 | Reinke et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,205,243 B1 | 3/2001 | Migdal et al. |
| 6,210,162 B1 | 4/2001 | Chishti et al. |
| 6,217,325 B1 | 4/2001 | Chishti et al. |
| 6,217,334 B1 | 4/2001 | Hultgren et al. |
| 6,227,850 B1 * | 5/2001 | Chishti .................. A61C 7/00 |
| | | 433/213 |
| 6,244,861 B1 | 6/2001 | Andreiko et al. |
| 6,250,918 B1 | 6/2001 | Sachdeva et al. |
| 6,261,248 B1 | 7/2001 | Takaishi et al. |
| 6,283,761 B1 | 9/2001 | Joao |
| 6,309,215 B1 | 10/2001 | Phan et al. |
| 6,315,553 B1 * | 11/2001 | Sachdeva ............... A61C 7/00 |
| | | 433/213 |
| 6,318,994 B1 | 11/2001 | Chishti et al. |
| 6,322,359 B1 | 11/2001 | Jordan et al. |
| 6,350,119 B1 | 2/2002 | Jordan et al. |

(56) References Cited

U.S. PATENT DOCUMENTS

| | | |
|---|---|---|
| 6,350,120 B1 | 2/2002 | Sachdeva et al. |
| 6,371,761 B1 | 4/2002 | Cheang et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,422,864 B1 | 7/2002 | Glatt |
| 6,431,870 B1 * | 8/2002 | Sachdeva ............ A61C 9/0046 433/213 |
| 6,463,344 B1 | 10/2002 | Pavloskaia et al. |
| 6,464,496 B1 | 10/2002 | Sachdeva et al. |
| 6,471,512 B1 | 10/2002 | Sachdeva et al. |
| 6,482,298 B1 | 11/2002 | Bhatnagar et al. |
| 6,524,101 B1 | 2/2003 | Phan et al. |
| 6,540,512 B1 | 4/2003 | Sachdeva et al. |
| 6,554,611 B2 | 4/2003 | Shishti et al. |
| 6,572,372 B1 | 6/2003 | Phan et al. |
| 6,575,751 B1 | 6/2003 | Lehmann et al. |
| 6,587,828 B1 | 7/2003 | Sachdeva |
| 6,616,444 B2 | 9/2003 | Andreiko et al. |
| 6,629,840 B2 | 10/2003 | Chishti et al. |
| 6,632,089 B2 | 10/2003 | Rubbert et al. |
| 6,633,789 B1 | 10/2003 | Nikolskiy et al. |
| 6,705,863 B2 | 3/2004 | Phan et al. |
| 6,722,880 B2 | 4/2004 | Chishti et al. |
| 6,757,898 B1 | 6/2004 | Ilsen et al. |
| 6,776,614 B2 | 8/2004 | Wiechmann et al. |
| 7,027,642 B2 | 4/2006 | Rubbert et al. |
| 7,107,226 B1 | 9/2006 | Cassidy et al. |
| 7,156,655 B2 | 1/2007 | Sachdeva et al. |
| 10,332,164 B2 | 6/2019 | Abolfathi et al. |
| 2002/0006597 A1 | 1/2002 | Andreiko et al. |
| 2002/0015934 A1 | 2/2002 | Rubbert et al. |
| 2002/0025503 A1 | 2/2002 | Chapoulaud et al. |
| 2002/0042038 A1 | 4/2002 | Miller et al. |
| 2002/0048741 A1 | 4/2002 | Jordan et al. |
| 2002/0156652 A1 | 10/2002 | Sachdeva et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer et al. |
| 2004/0002873 A1 | 1/2004 | Sachdeva et al. |
| 2004/0073417 A1 | 4/2004 | Rubbert et al. |
| 2004/0115586 A1 | 6/2004 | Andreiko et al. |
| 2004/0128010 A1 | 7/2004 | Pavlovskaia et al. |
| 2005/0055118 A1 | 3/2005 | Nikolskiy et al. |
| 2005/0084826 A1 * | 4/2005 | Pilaro ...................... A61C 5/00 433/215 |
| 2005/0159986 A1 | 7/2005 | Breeland et al. |
| 2019/0244264 A1 | 8/2019 | Abolfathi et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | 08508174 | 9/1996 |
| JP | H08508174 A | 9/1996 |
| WO | WO-9008512 A1 | 8/1990 |
| WO | WO-9104713 A1 | 4/1991 |
| WO | WO-9115163 A1 | 10/1991 |
| WO | WO-9410935 A1 * | 5/1994 ......... A61C 13/0004 |
| WO | WO-9815227 A1 | 4/1998 |
| WO | WO-9832394 A1 | 7/1998 |
| WO | WO-9844865 A1 | 10/1998 |
| WO | WO-9858596 A1 | 12/1998 |
| WO | WO-0147405 A2 | 7/2001 |

OTHER PUBLICATIONS

A System for Human Jaw Modeling Using Intra-Oral Images, Sameh M. Yamany and Aly A. Farag Computer Vision and Image Processing Laboratory University of Louisville, Proceedings of the 20th Annual International Conference of the IEEE Engineering in Medicine and Biology Society, vol. 20, No. 2,1998 (Year: 1998).*
ip.com search, Mar. 9, 2022 (Year: 2020).*
AADR. American Association for Dental Research, Summary of Activities, Mar. 20-23, 1980, Los Angeles, CA, p. 195.
Alcaniz, et al., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin, in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253(1984).
Biggerstaff, "Computerized Diagnostic Setups and Simulations," Angle Orthod., 40(1):28-36 (Jan. 1970).

(56) References Cited

OTHER PUBLICATIONS

Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL < http://astronomy.swin.edu.au/—pbourke/prolection/coords > .
Boyd et al., "Three Dimensional Diagnosis and Orthodontic Treatment of Complex Malocclusions With the Invisalign Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at < http://www.cardinalpaint.com > on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, Part 3 The Computer Gives New Vision—Literally,"Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004 < http://reference.com/search/search?q=gingiva > .
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at < http://www.dent-x.com/DentSim.htm > , 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet: < http://wscg.zcu.cz/wscg98/papers98/Strasser 98.pdf, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Google patents search, 'dentistry and web browser and viewer and plug in' Sep. 3, 2015. 2 pages.
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxillofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Interneton Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informationen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).

(56) References Cited

OTHER PUBLICATIONS

Important Tip About Wearing the Red White & Blue Active Clear Retainer System. Allesee Orthodontic Appliances-Pro Lab. 1 page (1998).
JCO Interviews, "Craig Andreiko , DDS, MS on the Elan and Orthos Systems," JCO, pp. 459-468 (Aug. 1994).
JCO Interviews, "Dr. Homer W. Phillips on Computers in Orthodontic Practice, Part 2," JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Clin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "PROCERA Research Projects 1993 —Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & Ars Materials, Inc., Raintree Essix, Technical Magazine Table of contents and Essix Appliances, < http://www.essix.com/magazine/defaulthtml > Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System In Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolaryngol Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Spallek, et al. Web-based 3D online crown preparation course for dental students. Department of Dental Informatics and Department

(56) References Cited

OTHER PUBLICATIONS of Restorative dentistry, Temple University School of Dentistry, Philadelphia, USA, University of Applied science, Germany. Sep. 3, 2015. 5 pages.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice Is Clear: Red, White & Blue . . . The Simple, Affordable, No. Braces Treatment, Allesee Orthodontic Appliances-Pro Lab product information, 6 pages (2003).

The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml, 5 pages (May 19, 2003).

The Choice is Clear: Red, White & Blue . . . The Simple, Affordable, No-Braces Treatment, Allesee HJ Orthodontic Appliances-Pro Lab product information for patients, (http://ormco.com/aoa/appliancesservices/RWB/patients.html), 2 pages (May 19, 2003).

The Red, White & Blue Way to Improve Your Smile!, Allesee Orthodontic Appliances-Pro Lab product information for patients, 2 pages (1992).

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden, "A New Method to Determine Tooth Positions and Dental Arch Dimensions," J. Dent. Res., 51(4):1104 (Jul.-Aug. 1972).

Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993).

Varady et al., "Reverse Engineering Of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 388-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL(http://wscg.zcu.cz/wscg98/wscg98.h).

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be A Candidate For This Invisible No-Braces Treatment, Allesee Orthodontic Appliances-Pro Lab product information for patients, 2 pages (2002).

Doyle, "Doctors use CAD/CAM to take the pain out of excessive dental procedures," [online], [retrieved on Sep. 18, 2002]. Retrieved from the Internet< URL: http://cgw.pennnet.com/Articles/Article_Display.cfm?Section=Archives&Subsection=Display&ARTICL E ID=835188,KEYWORD=digital%20dentistry>.

Orthocad, Summer Newsletter, "Wired in 3D," Sep. 10, 2001.

Arnold et al., "Virtual teeth for endodontics training and practice," 2000 IEEE Conference on Information Visualization. An International Conference on Computer Visualization and Graphics, London, UK, pp. 597-604 (2000).

\* cited by examiner

HEALTH-CARE SYSTEMS AND METHODS

CROSS-REFERENCE

This application is a continuation application of U.S. patent application Ser. No. 11/033,097, filed Jan. 11, 2005, which is incorporated herein by reference in its entirety. U.S. application Ser. No. 10/205,026, filed Jul. 23, 2002, and U.S. application Ser. No. 09/534,461, filed Mar. 24, 2000, are incorporated herein by reference in their entirety.

BACKGROUND

The Internet has become a significant medium for communication and commerce and has enabled millions of people to share information and conduct business electronically. The unique characteristics of the Internet, such as its ability to provide enhanced communication, rich text, and graphic environment, provide an ideal support for a wide variety of electronic commerce transactions. For example, a consumer can search, review, and extensively shop a number of competing chains in an instant. As such, consumers benefit by being able to obtain a good price relatively quickly and easily.

On-line retailers also benefit, since these retailers can carry a larger number of products at a lower cost and with greater merchandising flexibility without the physical constraints faced by traditional retailers. Additionally, they can assist the consumer's purchase decision by providing relevant information and enabling consumers to shop at their convenience by remaining open 24 hours a day, seven days a week. Online retailers can also provide personalized services and use direct marketing efforts based on information provided by customers.

As such, the Internet has evolved into a unique sales and marketing channel. The ubiquity and convenience of the Internet makes it ideal for dispensing information on certain topics that traditionally require visits to specialists. For example, certain consumers may be interested in products and services associated with orthodontics and dentofacial orthopedics that specializes in the diagnosis, prevention and treatment of dental and facial irregularities ("malocclusion" or "bad bite"). The orthodontic treatment process typically uses corrective appliances such as braces and/or other fixed or removable appliances to bring the teeth, lips and jaws into proper alignment and to achieve a facial balance. The pervasiveness of the Internet makes it an ideal source for information relating to these products and services.

SUMMARY

In one aspect, a virtual health-care electronic commerce community includes a network to communicate information relating to the community; one or more patients coupled to the network; one or more treating professionals coupled to the network; and a server coupled to the network, the server storing data for each patient and securely sharing health-care information for authorized professionals.

Implementations of the above aspect may include one or more of the following. The treating professional can view one or more of the following patient data visualization over the network: a right buccal view; a left buccal view; a posterior view; an anterior view; a mandibular occlusal view; a maxillary occlusal view; an overjet view; a left distal molar view; a left lingual view; a lingual incisor view; a right lingual view; a right distal molar view; an upper jaw view; and a lower jaw view. The treating professionals can include dentists or orthodontists working singly or in combination with other professionals. One or more partners can be connected to the network. The partners can be a financing partner, a supplier, or a delivery company. The treating professionals can perform office management operations using the server. The office management operations include one or more of the following: patient scheduling, patient accounting, and claim processing. The patients and the treating professionals can access the server using browsers. The treating professionals can share the patient's information with another authorized treating professional for consultations and assistance, among others.

In another aspect, a method for performing dental-related electronic commerce includes transmitting teeth data associated with a patient from a dental server to a treating professional computer over the Internet upon an authorized request; displaying a three-dimensional computer model of the teeth at the treating professional computer using a browser; allowing a treating professional to manipulate the three-dimensional computer model of the teeth using the browser or an application running on a patient computer; transmitting the computer model from the treating professional computer to the server; and generating an appliance to treat the patient based on the computer model of the teeth.

Implementations of the above aspect may include one or more of the following. The system can provide financing options for the patient using one or more financing partners. The system can offer an on-line shop geared to the patient's dental requirements and/or office needs/supplies. The system also allows a treating professional to manipulate the three-dimensional computer model of the teeth using the browser or an application running on a local computer and further comprises displaying a plurality of dental views.

A treating professional can manipulate the three-dimensional computer model of the teeth using the browser and may further comprise clicking on a tooth to adjust its position. The system can display x, y and z axes to allow the treating professional to adjust the position of the tooth. Treating professionals can show the models to other authorized professionals. Supplemental services can also be offered to the patient, including teeth whitening services.

In another aspect, a server supports a health-care electronic commerce community with one or more patients and one or more service providers. The server includes a processor adapted to communicate with a network; a data storage device coupled to the processor and adapted to store data for each patient; and software to communicate 3D patient data in response to a patient request.

Implementations can include one or more of the following. A browser can receive the patient request and can transmit the request to the server. The browser can use a viewer plug-in to visualize patient data in 3D. Alternatively, an application running on a local patient computer can visualize the patient data. The providers can provide health-care services such as dentistry applications, cosmetic augmentation, hair-care enhancements, liposuction, or plastic or reconstructive surgery.

Advantages of the system may include one or more of the following. The system supports a virtual community of dental patients, dentists, specialists such as orthodontists and oral surgeons, financial institutions, benefit providers and the providers of dental equipment or services. For treating professionals, such as dentists and orthodontists, the system provides a one-stop solution for planning patient treatments, managing communication with patients, storing patient records and sharing records with relevant persons outside the doctor's office, including for example, consulting professionals who advise the doctor of preferred treatment plans. The system can act as the repository for the file notes and visual imagery (photographs, x-rays and virtual treatment plans) associated with the course of treatment. The doctors can control access to the centralized patient file. Various tools are provided to support the interpretation of information and the diagnostic process. For example, the system allows doctors to retrieve and analyze patient information and to simulate present and potential patient dental structure using two and three-dimensional visual imagery of the patient's teeth and other anatomical structures. The system supports visualization of the expected outcome of a particular course of treatment. These images can enhance the patient's understanding of the benefits of treatment and can act as a valuable selling tool for the doctor. The system also provides diagnostic decision-support capabilities such as visualizing the placement of implantations, veneers and crowns before or after a course of treatment to straighten the teeth. The system provides an animated prediction of the suggested treatment that can help the patient and the doctor to visualize the pace of treatment. Using these tools, the doctor can easily and quickly view and/or edit the treatment plan. When doctor and patient choose the final treatment plan the system disseminates aspects of the plan and the relevant patient records to the appropriate members of the virtual community, thus reducing the cost and delay associated with traditional physical shipment of patient information. Aspects of the final treatment plan can be used to generate appliances used in the physical treatment. The information associated with the patient's treatment (visual images, virtual treatment plans, file notes and the like) are digitized and maintained in a central storage facility in a secure manner. Doctors and patients can have access to these files without the need to extract files and models from storage and with reduced risk of records being misplaced.

Administratively, the system allows a dental office to be managed more efficiently without requiring the treating professional to purchase and maintain special software. The system keeps track of all patients that need to be contacted for an appointment. Scheduling can be done automatically or can be customized to the office's preference and availability of treating professionals and supporting resources. Based on the appointments, the system can electronically mail (email) patients with reminders. Alternatively, the system can print reminder cards that can be mailed to patients reminding them of their appointment. The system can also automatically generate personalized correspondence to patients relating to data collected in the initial exam and treatment recommendations. Moreover, the patient can review the treatment proposed by the treating professional anywhere.

The system also simplifies and streamlines the processing of insurance claims to produce an orderly flow of information. Insurance claims can flow through the treating professional's office from pre-authorization to continuation of treatment with a minimal amount of intervention. The system also provides accounting functions to check out patients, post charges, setup contracts, add comments to ledgers, post payments, adjust ledgers, and display all transactions applied to specific ledgers.

Moreover, treating professionals can leverage the collective purchasing power of the system by being able to order supplies required or requested by patients directly through the system at a discount. These supplies can be directly shipped to the patients, thus avoiding overhead costs associated with handling the supplies. Further, information reviewed or generated by the treating professionals is provided through a secure on-line connection. Thus, the patient's privacy as well as the treating professional's sensitive office information is not compromised.

For patients, the system provides a broad array of dental-care resources that help consumers find answers to their critical dental questions and make informed purchasing decisions. The system also enables people to share their experiences and to support one another in managing their medical conditions. This is done through forums where Internet users with interests and concerns about their dental health can interact with each other, to interact in a community environment and to access content created by others.

The system is convenient to use and provides informative shopping experience through which dental care services and dental-related products can be dispensed. Consumers can access the system using an intuitive, easy-to-use shopping interface that is available 24 hours a day, seven days a week. Consumers can shop quickly and conveniently from anywhere Internet access is available. A customer can store his or her dental history and other relevant dental information, as well as create personalized shopping lists for quick and easy reordering of his or her dental supplies.

BRIEF DESCRIPTION OF THE DRAWINGS

Other advantages will be apparent from the description that follows, including the figures and claims, in which:

DESCRIPTION

Figure 1:
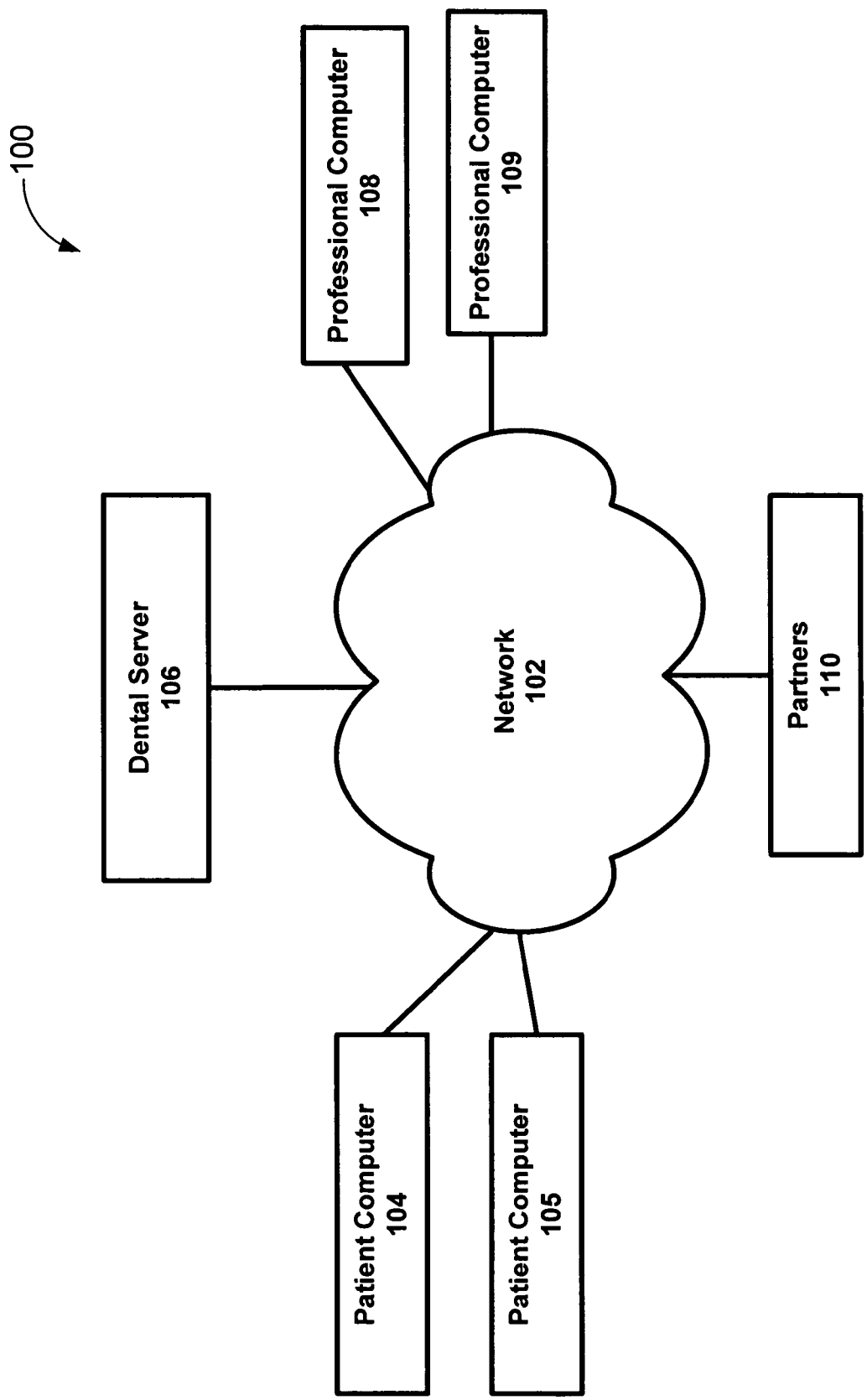
FIG. 1 is a diagram of an exemplary environment supporting electronic commerce.

Referring now to FIG. 1, an environment supporting a dental system 100 is shown. The system 100 communicates over a network 102 that can be a local area network or a wide area network such as the Internet.

One or more patient computers 104-105 can be connected to the network 102. In one embodiment where the network 102 is the Internet, the patient computers execute a suitable browser such as Navigator® from Netscape, Inc. or Internet Explorer® from Microsoft Corp. By clicking on the highlighted text (or specific graphic image), the user can jump from the current web page to a new web page address associated with the link—with the new page displayed on the screen. In this manner, the user can "surf the web" by clicking on an almost endless succession of links going to page after page all following a common thread as defined by the text or graphic component of the link label.

Through the network 102, the patient computers 104-105 can access a health server, for example a dental server 106 that houses dental information. The dental server 106 serves a web site, a portal, a vortal (vertical portal), or a content site for providing dental-related information to interested parties such as dental patients, dentists, orthodontists, and others. When sensitive information is communicated through the dental server 106, such information may be securely encrypted using Secure Socket Layer ("SSL") technology throughout the transaction. The server 106 can be a standalone computer or can be a server farm that can distribute processing and communication activity across a computer network so that no single device is overwhelmed. During load balancing, if one server is swamped with requests, excess requests are forwarded to another server with more capacity.

The network 102 connects the dental server 106 to one or more treating professional workstations 108-109. The workstations 108-109 allow treating professionals access to a plethora of services provided by the dental server 106 such as patient treatment and office management, among others. The dental server 106 stores information associated with patient history on-line in a secure manner and also provides the treating professional a comprehensive view of the patient's treatment history at any time using a suitable browser, eliminating the need to pull treatment files or charts or to search for misfiled or lost charts. The dental server 106 also provides treating professionals with tools to analyze patient data, for example, tools to reconstruct a 3D model or rendering of the patient's teeth. For example, using the browser, the treating professional can request the dental server 106 to animate the progress of the treatment plan. When the treating professional arrives at a prescription or other final designation or diagnosis, the treatment prescription is used to automatically generate appliances, as described in more detail below. Further, in addition to aiding treating professionals in treating patients, the software allows the treating professional to perform office management, purchasing and other logistical operations using the browser and the dental server 106.

In addition to communicating with patients and treating professionals, the dental server 106 can communicate with one or more partners 110 using the network 102. The partners 110, can be product suppliers, service providers, or any suitable commercial entities.

For example, one partner 110 can be a financing partner that offers customers one or more electronic financing options. In one implementation, the financing partner can be a credit card processing company. The credit card processing company can accept a customer's existing credit card or can issue the customer with a new credit card. Further, the credit card can be issued under the name of a third-party bank, the name of the credit card processing company, or the name of the site supported by the dental server 106 under a co-branding arrangement.

The customer enters the sensitive data such as credit card number, shipping address, among others, onto a purchase form. The credit data is then submitted, collected and passed securely through the dental server 106, e.g., using SSL. This data can be processed in real-time online or can be collected by mail or telephone and then entered by an operator. A processor at the credit card processing company then verifies that the credit card number is valid and is not stolen, among other anti-fraud measures. If the credit card information is valid, the purchase price will be reserved from the issuing bank of the consumer's credit card and allocated to the account associated with the server 106. Periodically, the credit card processor settles all accounts; it is at this time that all monies move. Funds reserved are transmitted from the issuing bank of the cardholder's credit card to the account of the server 106. Also, discount fees are paid from these funds, as they are moving.

Alternatively, the financing partner can debit from the customer's checking account over the Internet. One such check debiting services is the MerchanTrust™ Paperless Checks™ Services, available from Merchant Commerce, Inc. These services provide customers with the convenience of making online purchases by checking account debits, with no manual data entry required of a merchant. In this embodiment, a customer fills in a form at the site with bank information printed at the bottom of his or her personal check. The information is processed as an Electronic Funds Transfer (EFT) to the customer's account using the Automated Clearinghouse (ACH) payment system.

Yet another possible partner 110 is a dental supply retailer providing an on-line shop on the web site to retail dental products to the customers and treating professionals. The retailer can be a co-branding partner that uses the brand name linked or suitably associated with the web site of the server 106 such that users of the server 106 would not know that the on-line shop is actually operated by a third party. The retailer can offer dental products for brushing, flossing, and cleaning of dental implants and bridges. Other dental products include anti-plaque rinse and plaque-fighting toothpaste. The retailer can also sell other health-care-related products such as prescription drugs; non-prescription drugs; personal care products; beauty and spa products; vitamins; herbs and nutrition; and medical supplies. Additionally, the retailer can serve the needs of the treating professionals by offering products such as brackets, buccal tubes, bands, archwire products, bonding adhesives, hand instruments, systems, supplies and equipment.

Yet another partner 110 can be a shipping partner. The shipping partner delivers dental supplies or goods received from a multiplicity of producers and manufacturers for ultimate distribution to each customer. The facilities for warehousing and introduction of goods into a transportation stream for redistribution are the so-called "cross-docking" facilities. The article of supply or good flows in bulk from a producer or a manufacturer to one or more cross-docking facilities owned by either the shipping partner or the operator of the server 106. The items are then be broken into smaller unit sizes and distributed to the customers.

The above list of partners lists only exemplary partners and is not an exhaustive list. Other possible partners include value-added service providers such as third party software providers who provide plug-in viewing and diagnostic enhancements that can be used by the professionals.

The dental server 106 can perform dynamic targeting and information gathering. The users provide demographic information when they register for the service, and the dental server 106 can track the users' behavior the entire time they are online. As a result, the dental server 106 can deliver targeted advertisements and can further measure their effectiveness. As examples, users can receive ads from a brokerage firm when they are viewing sites containing stock quotes or financial news, or receive promotions from a bookseller when browsing sites containing book reviews. As such, the dental server 106 can provide a prominent and sustained advertising medium to the community. In contrast to most portal and content sites which display advertising, the site remains with users the entire time they are online. Once users are logged on, the site remains in full view throughout the session, including when they are waiting for pages to download, navigating the Internet, or even engaging in non-browsing activities such as sending or receiving e-mail. The constant visibility of the site allows advertisements to be displayed for a specified period of time.

In combination, the dental server 106 forms a hub that links dental patients using patient computers 104-105, treating professionals using workstations 108-109, and partners 110 into a living electronic commerce (e-commerce) community.

Figure 2:
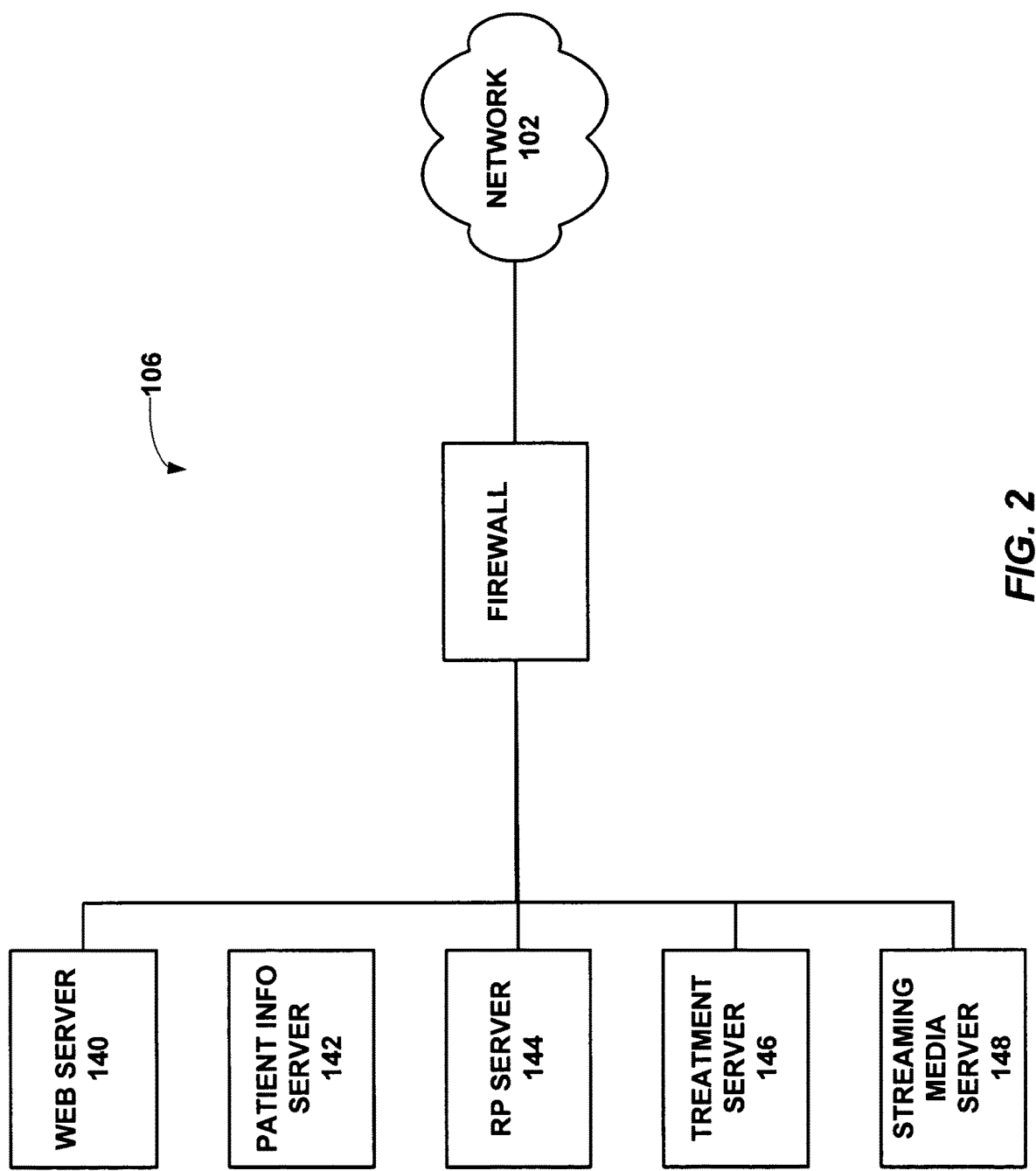
FIG. 2 is a diagram of a server structure and corresponding link to a network, such as the internet, to support electronic commerce within the context of an embodiment of the invention.

FIG. 2 shows an embodiment of the dental server 106. The dental server 106 includes a web server 140, a patient information server 142, a resource planning (RP) server 144, a treatment server 146 and a streaming media server 148. In one embodiment, the RP server 144 runs Microsoft SQL server and provides information relating to a doctor or a patient such as address and history. When a patient's case or a static snapshot of the case is needed, the data is pulled from the patient information server 142. When media data, such as video, needs to be streamed to a requesting viewer such as a doctor or a patient, the streaming media server 148 can send the stream. In one implementation, the streaming data is stored in QuickTime format on a Linux-based server running the QuickTime server software.

The servers can be clustered. In one embodiment using Microsoft's Cluster Server, cluster-enabled applications such as Microsoft's SQL Server and Exchange may be employed. With Cluster Server, two servers can run applications at the same time. When one server fails, the remaining server handles its application as well as the failed server's applications. Next, the remaining server adopts the IP address of the failed server and mounts one or more data drives that the two systems share. The remaining server is rebooted and applications such as SQL Server can be restarted and reinitialized on this server. Persistent viewers can re-attach to the server and continue to operate.

Figure 3:
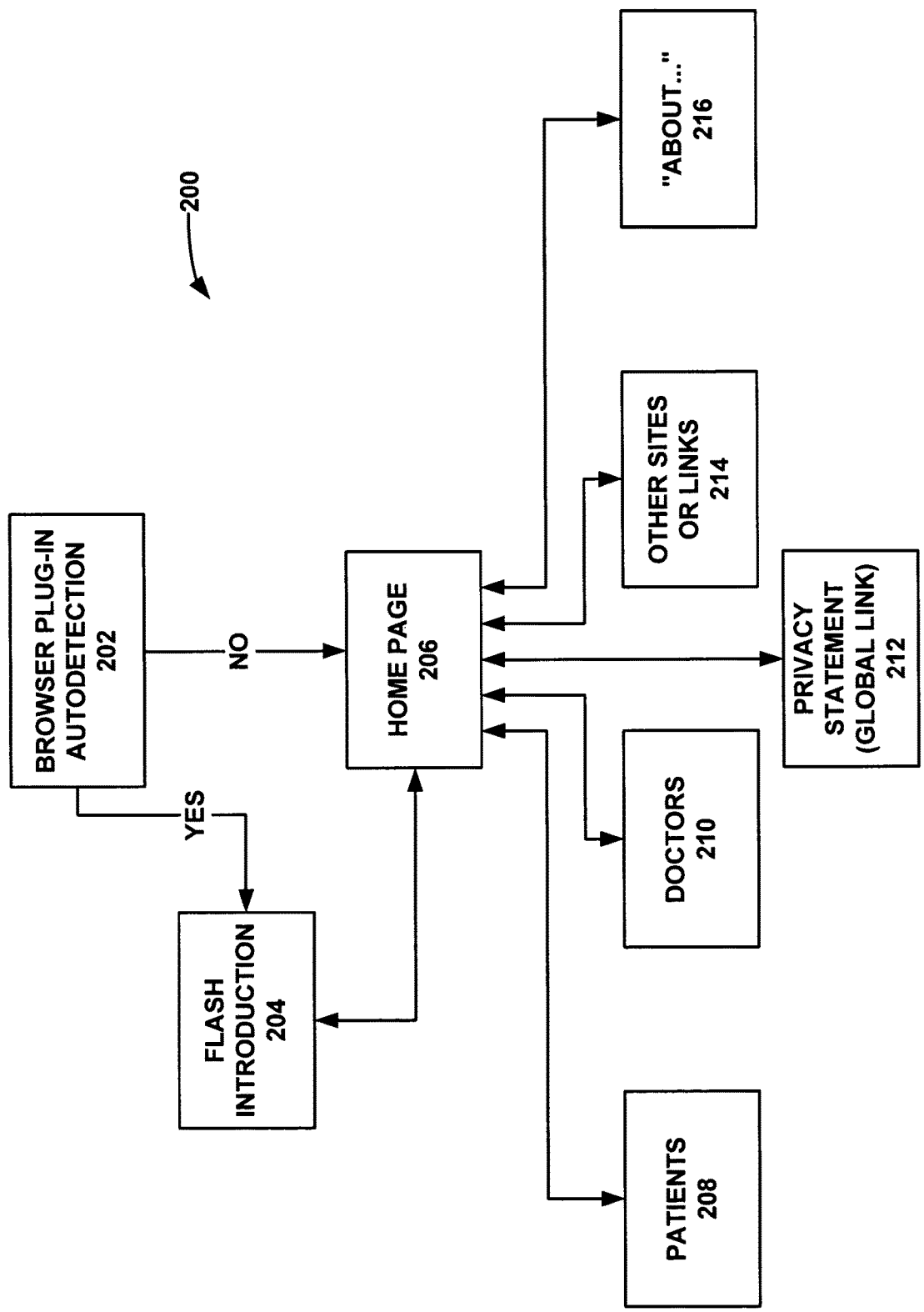
FIG. 3 is a structural diagram of a web site that may run on the server of FIG. 2.

Referring now to FIG. 3, a diagram 200 shows various major functions supported by the dental server 106. First, the process 200 may perform an automatic detection for the existence of a browser welcome plug-in (step 202). If the welcome plug-in exists, an introductory animation (Flash) is shown to the viewer (step 204). From step 202 or 204, the process 200 shows a home page (step 206) with one or more links. A link is created by having a word in a text field (or a graphic image on a web page) linked to the location of another web page via a string of information setting forth the new web page address presented in hypertext transfer protocol (I-ITTP), among others.

The user can navigate the home page to join a particular site from a constellation of related sites. For instance, the user can navigate to a patient's site (step 208), a doctor's site (step 210), a privacy statement site (step 212), one or more additional sites or links (step 214), and an "About" site (step 216), among others. The additional sites can be an on-line shopping store that is co-branded with the web site hosted by the server 106, or the on-line shopping store can be directly affiliated with a third party such as planet-rx.com, among others. The additional sites can also be third party value-added providers of products and/or services.

Figure 4:
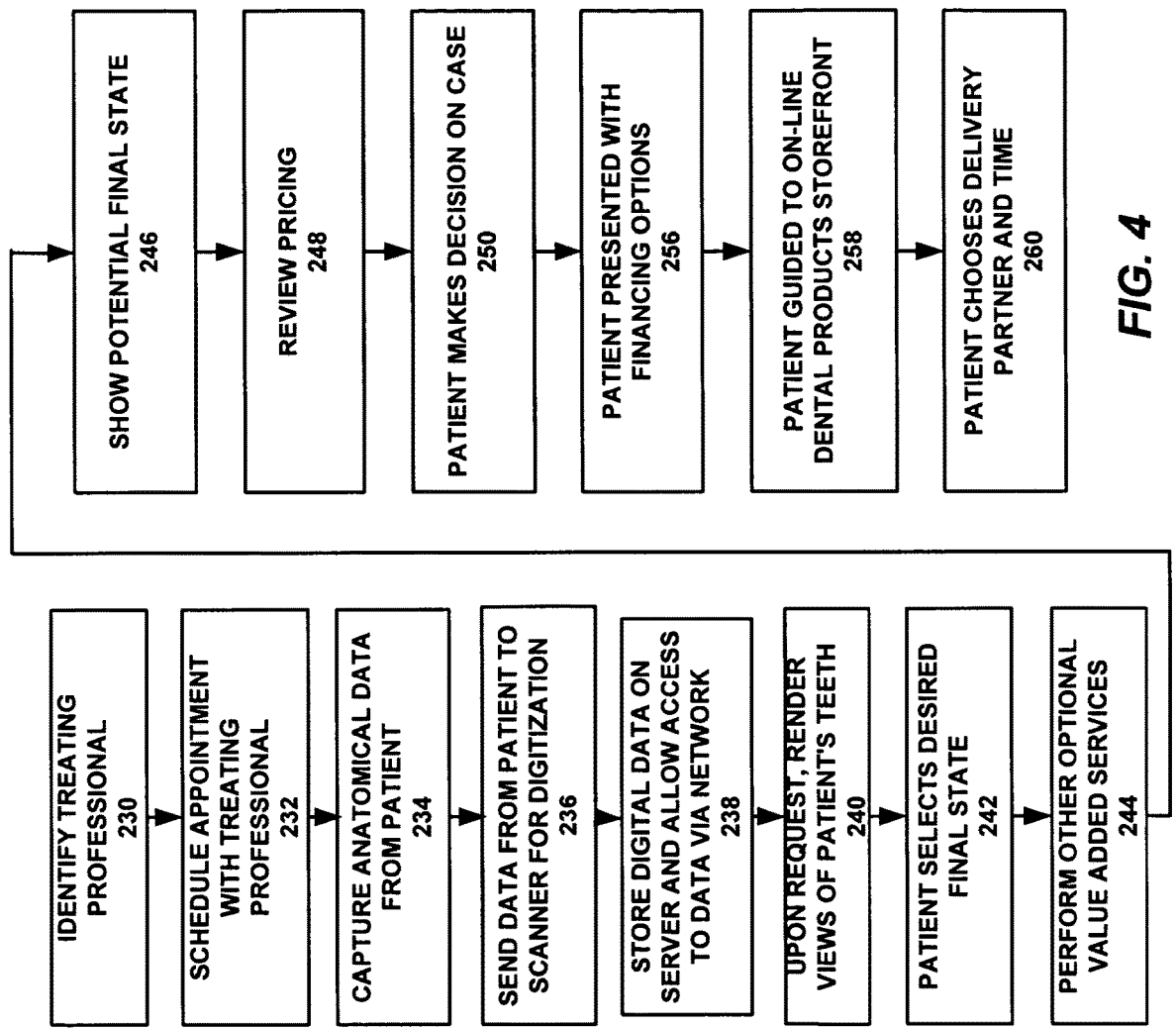
FIG. 4 is a flowchart of a process for selecting dental services, from the perspective of a patient.

FIG. 4 illustrates an exemplary usage of the system of FIG. 1 from a patient's perspective. First, a prospective patient using a patient computer 104 visits the web site on the dental server 106 and identifies a treating professional meeting one or more criteria (step 230), for example, a professional whose location is closest to his or her home address. Next, the patient schedules an appointment with the treating professional (step 232). At the meeting, an assistant captures various anatomical data from the patient by taking digital photographs of the face and teeth, taking x-rays of the front, back, side, and top/bottom of the patient, taking one or more impressions, among others (step 234). Next, certain or all of this information is entered into a form on the server 106. The data is then digitized (step 236), stored on the dental server 106, and made available to treating professionals and the patient over the Internet (step 238). Next, the server 106 and one or more orthodontic treating persons process the patient data and render the patient's teeth in a plurality of alternative final states (step 240). Based on the choices, the patient selects a desired final state (step 242).

In addition to performing orthodontic operations, the dental server 106 can also perform other value-added services (step 244). For example, processes executed by the dental server 106 can simulate the color of the patient's enamel and show the color of the teeth before and after bleaching. Further, processes on the dental server 106 can simulate the color of the patient's silver fillings (amalgam) and show the teeth after cosmetic work to cover the amalgam (step 246). After visualizing the effects of the operations, comparing the before and after operations, and reviewing guideline pricing (step 248) for the orthodontic operation as well as add-ons such as bleaching, the patient makes a decision on the case (step 250).

Once the patient has accepted a particular treatment selection, the dental server 106 offers the patient with one or more financing options from one of its financial partners (step 256). Additionally, the dental server 106 can guide the patient to an on-line shopping store to purchase products relating to his or her dental health (step 258). For example, the patient can buy cleaning supplies, brushes, and flossing supplies at a price competitive to his or her traditional stores. Moreover, the products can be delivered to the patient using one or more delivery partners at a convenient time (step 260).

Figure 5:
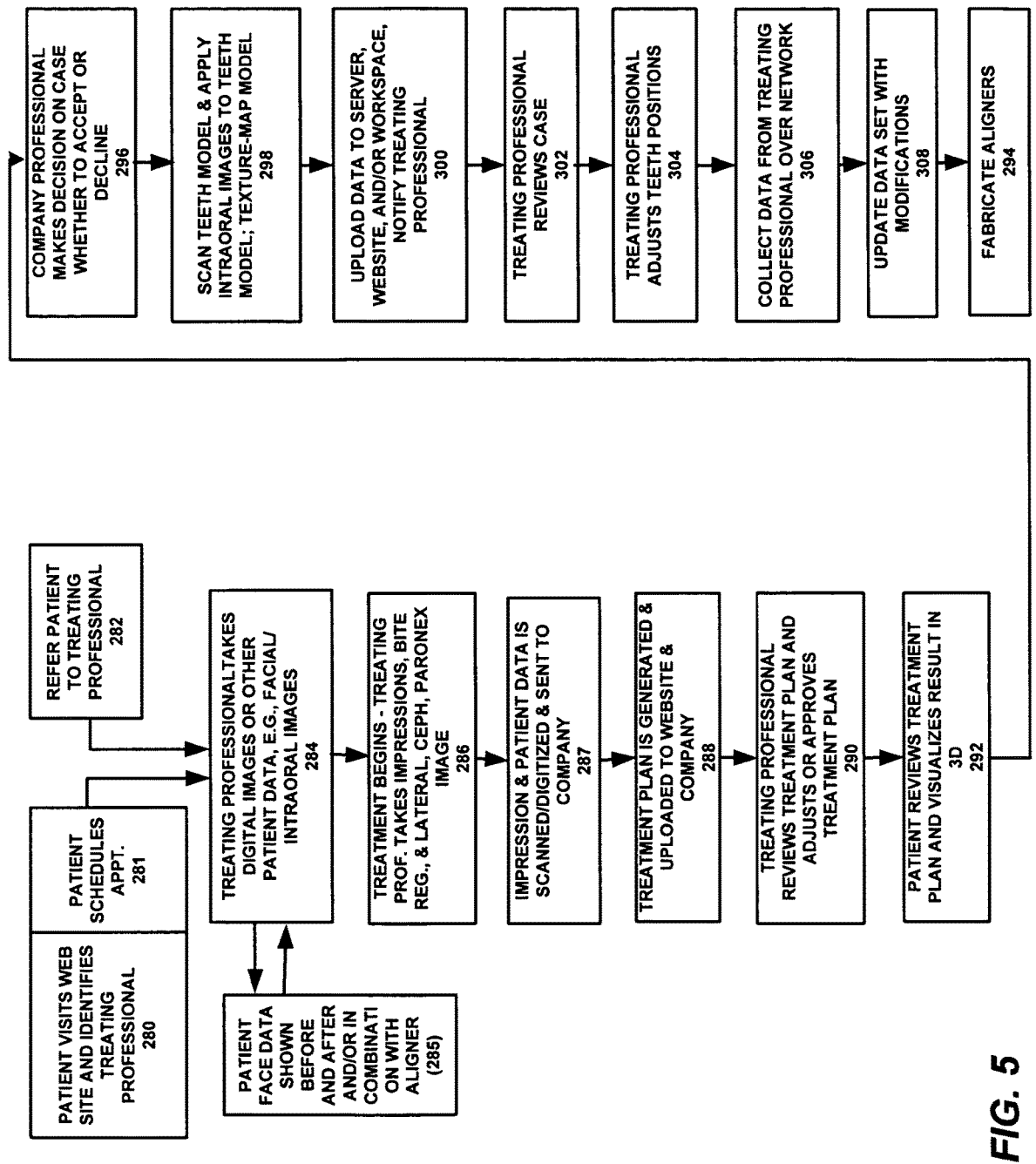
FIG. 5 is a flowchart of a process for providing dental services, from the perspective of a treating professional.

FIG. 5 illustrates an exemplary usage of the system of FIG. 1 from a treating professional's perspective. A prospective patient uses a patient computer 104 and visits the web site on the dental server 106 (step 280). The patient identifies a treating professional and schedules an appointment with the treating professional (step 281). Alternatively, a referring dentist can refer the patient to the treating professional.

The referring dentist can visit the website on the dental server 106 and use one or more dental esthetic tools to show patients the potential benefits of treatment, e.g., anterior and posterior esthetic restorations, and if the patient is interested, refers the patient to the treating professional (step 282).

During an initial examination, the treating professional or an assistant may take, e.g., a set of digital facial and intraoral images which is uploaded to a secure, collaborative workspace on the dental server 106 (step 284). The workspace is shared with the referring dentist.

Next, the treating professional generates a dentofacial treatment visualization showing the patient's face and smile before and after treatment. The treating professional can also combine the patient's face and an aligner into the intraoral image to show how inconspicuous the appliance will be (step 285).

Once the patient requests treatment, the treating professional takes impressions and a bite registration and sends the information to the company (step 284). The treating professional may also capture other data, such as by taking a lateral ceph and a panorex (step 286), and upload them to the company and/or workspace and/or website (287). The treating professional may also generate or create a treating prescription or plan and upload the same to the company and/or website and/or to the workspace (step 288). At any time, the treating professional may review the treatment plan and adjust or approve the same (step 290). The professional's assistant creates a separate workspace for the patient, uploads selected "before and after" images to the company and/or workspace and/or website and invites the patient to review the images (step 292). The aligners may then be accordingly fabricated as described below.

At the company, another professional reviews the records and decides to accept or decline the case (step 296). If accepted, the models are scanned, and the intraoral images are retrieved and used to texture-map enamel and gingiva (step 298). The data is then sent to the company and/or workspace and/or website and the treating professional is notified (step 300).

In one embodiment, the tooth models may be posted on a hypertext transfer protocol (http) web site for limited access by the corresponding patients and treating clinicians. Since realistic models have a large volume of data, the storage and transmission of the models can be expensive and time-consuming. To reduce transmission problems arising from the large size of the 3D model, in one embodiment, data associated with the model is compressed. The compression is done by modeling the teeth meshes as a curve network before transmission to the treating professional or website. Once the curve network is received, the 3D model is reconstructed from the curve network for the treating professional to analyze. More information on the compression is disclosed in U.S. Pat. No. 6,633,789, issued Oct. 14, 2003, entitled "EFFICIENT DATA REPRESENTATION OF TEETH MODEL", the contents of which are hereby incorporated by reference in their entirety.

The treating professional can, at his or her convenience, check the setup, and review the information sent in step 300 (step 302). The treating professionals can use a variety of tools to interpret patient information. For example, the treating professional can retrieve and analyze patient information through a reconstructed 3D model of the patient's teeth and other anatomical structures. The professional can view animations showing the progress of the treatment plan to help the treating physician visualize the pace of treatment. Using these tools, the treating professional can easily and quickly view and/or edit the treatment plan.

If necessary, the treating professional can adjust one or more teeth positions at various intermediate stages of treatment (step 304). A variety of diagnostic decision-support capabilities such as automated teeth collision detection can be used to aid the treating professional in adjusting the teeth positions.

When the treating professional arrives at a prescription or other final designation, the treatment information is automatically collected by the system over the Internet, thus eliminating the cost and delay associated with the traditional physical shipping of patient information (step 306). These modifications are then retrofitted onto the dataset used to generate the aligners (step 308). The aligners may then be physically fabricated (step 294).

Figure 6:
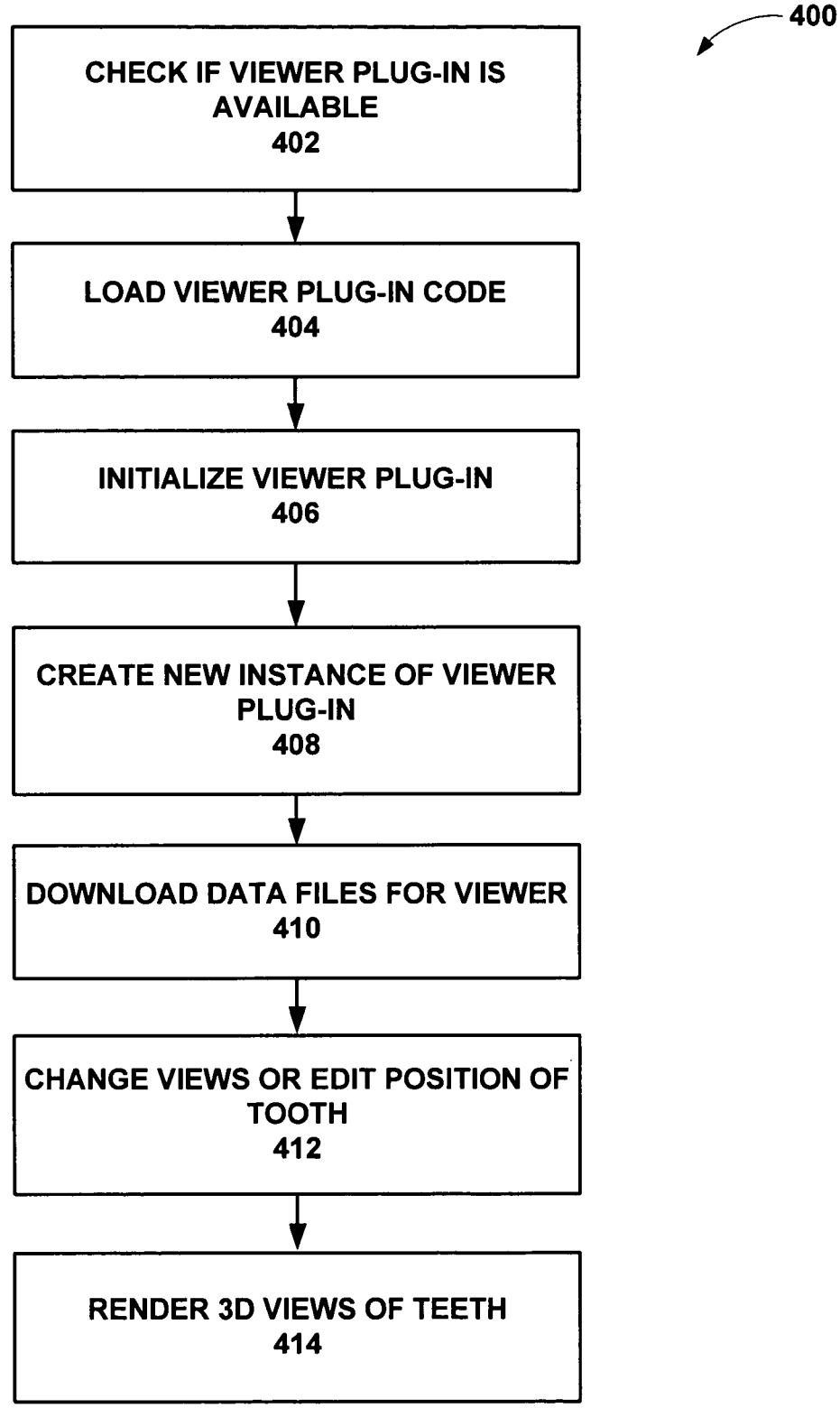
FIG. 6 is a flowchart of a process to render 3D views of a patient's teeth on a browser.

FIG. 6 shows a process 400 associated with a viewer that allows the treating professional to visualize the patient's teeth over the network 102 such as the Internet. In one embodiment, during start-up, a browser checks for a viewer plug-in module embodying the process 400 in a "plugins" subdirectory (Windows) or Plug-ins folder (Mac OS) in the same folder or directory as the browser (step 402). If the viewer plug-in module is available, the browser looks for a MIME type and extension info from the version resource. Through a TYPE attribute, the browser knows the MIME type and can load a registered plug-in first and, if there are no matches for the MIME type, the browser looks for a helper application.

Once the viewer plug-in is identified, the browser loads the viewer plug-in code into memory (step 404); initializes the viewer plug-in (step 406); and creates a new instance of the viewer plug-in (step 408). When the professional leaves the site or closes the window, the viewer plug-in instance is deleted. When the last instance of the viewer plug-in is deleted, the plug-in code is unloaded from memory.

Figure 7:
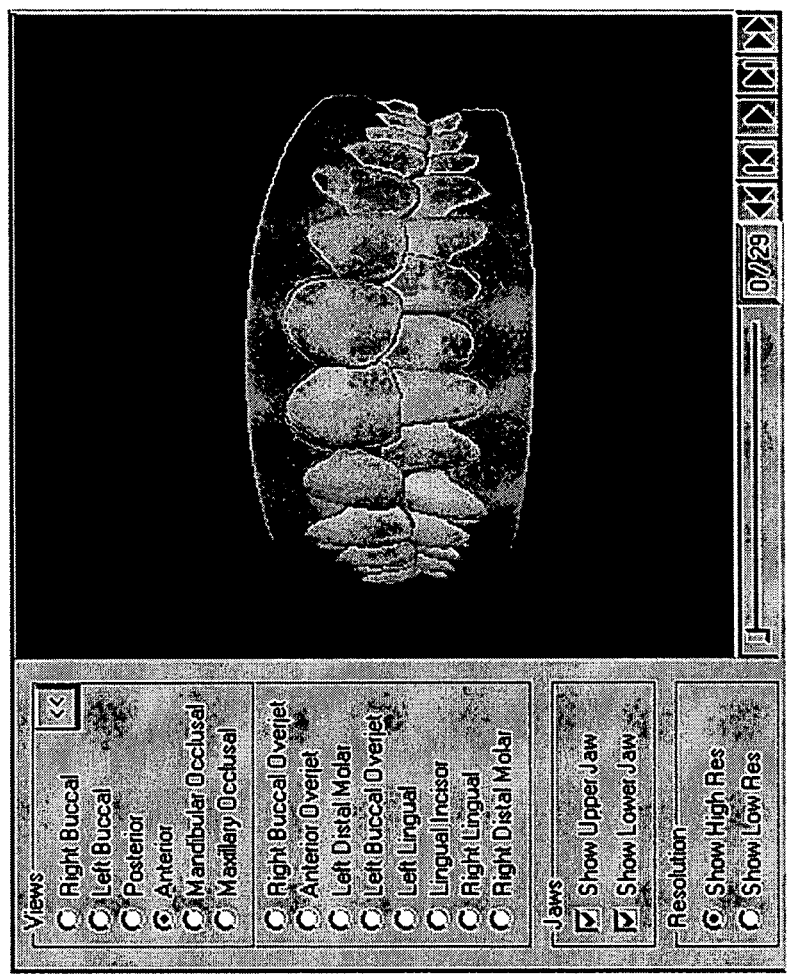
FIG. 7 is an exemplary output of the process of FIG. 6 using the browser.

Next, data files are downloaded to the viewer plug-in (step 410). In one implementation, the viewer plug-in downloads a data file from the dental server 102 using a suitable protocol such as a file transfer protocol (FTP). The viewer plug-in uses the downloaded file to present the treatment plan graphically to the clinician. The viewer plug-in also can be used by the treatment plan designer at the host site to view images of a patient's teeth. FIG. 7 shows an exemplary user interface for the viewer plug-in of FIG. 6. The professional can change views, select a particular tooth and change its position as desired (step 412).

3-D images of various orthodontic views can then be rendered after each instruction from the treating professional is received (step 414). In this process, an origin point, or "look from" point associated with a camera view is generated. Next, a "look at" point or a focus point associated with the camera view is determined. In this system, the line from LookFromPoint to LookAtPoint defines the direction the camera is shooting. Additionally, a camera Z vector, or up vector, is determined.

Figure 8:
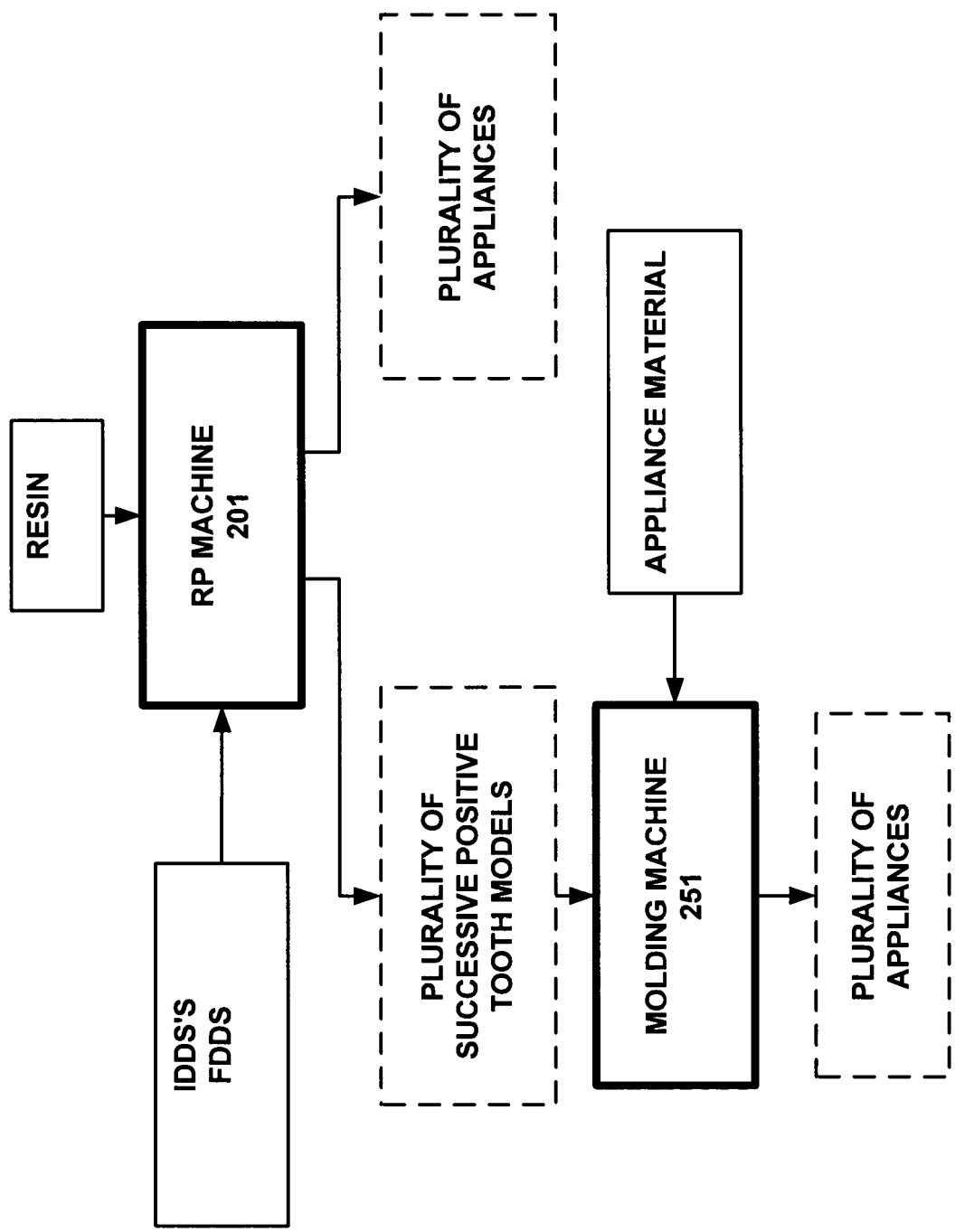
FIG. 8 is a diagram of a system for manufacturing appliances.

Once the intermediate and final data sets have been created, the appliances may be fabricated as illustrated in FIG. 8. Common fabrication methods employ a rapid prototyping device 201 such as a stereolithography machine. A particularly suitable rapid prototyping machine is Model SLA-250/50 available from 3D Systems, Valencia, Calif. The rapid prototyping machine 201 selectively hardens a liquid or other non-hardened resin into a three-dimensional structure which can be separated from the remaining non-hardened resin, washed, and used either directly as the appliance or indirectly as a mold for producing the appliance. The prototyping machine 201 receives the individual digital data sets and produces one structure corresponding to each of the desired appliances. Generally, because the rapid prototyping machine 201 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine 251 is used to produce the appliances from a more suitable material, such as 0.03 inch thermal forming dental material, available from Tru-Tain Plastics, Rochester, Minn. Suitable pressure molding equipment is available under the trade name BIOSTAR from Great Lakes Orthodontics, Ltd., Tonawanda, N.Y. The molding machine 251 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from a newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician can also form another set of plaster castings of the patient's teeth for digital imaging and manipulation. The clinician may wish to limit initial aligner production to only a few aligners, delaying production on subsequent aligners until the patient's progress has been evaluated and alignment configuration can be more accurately estimated.

Figure 9:
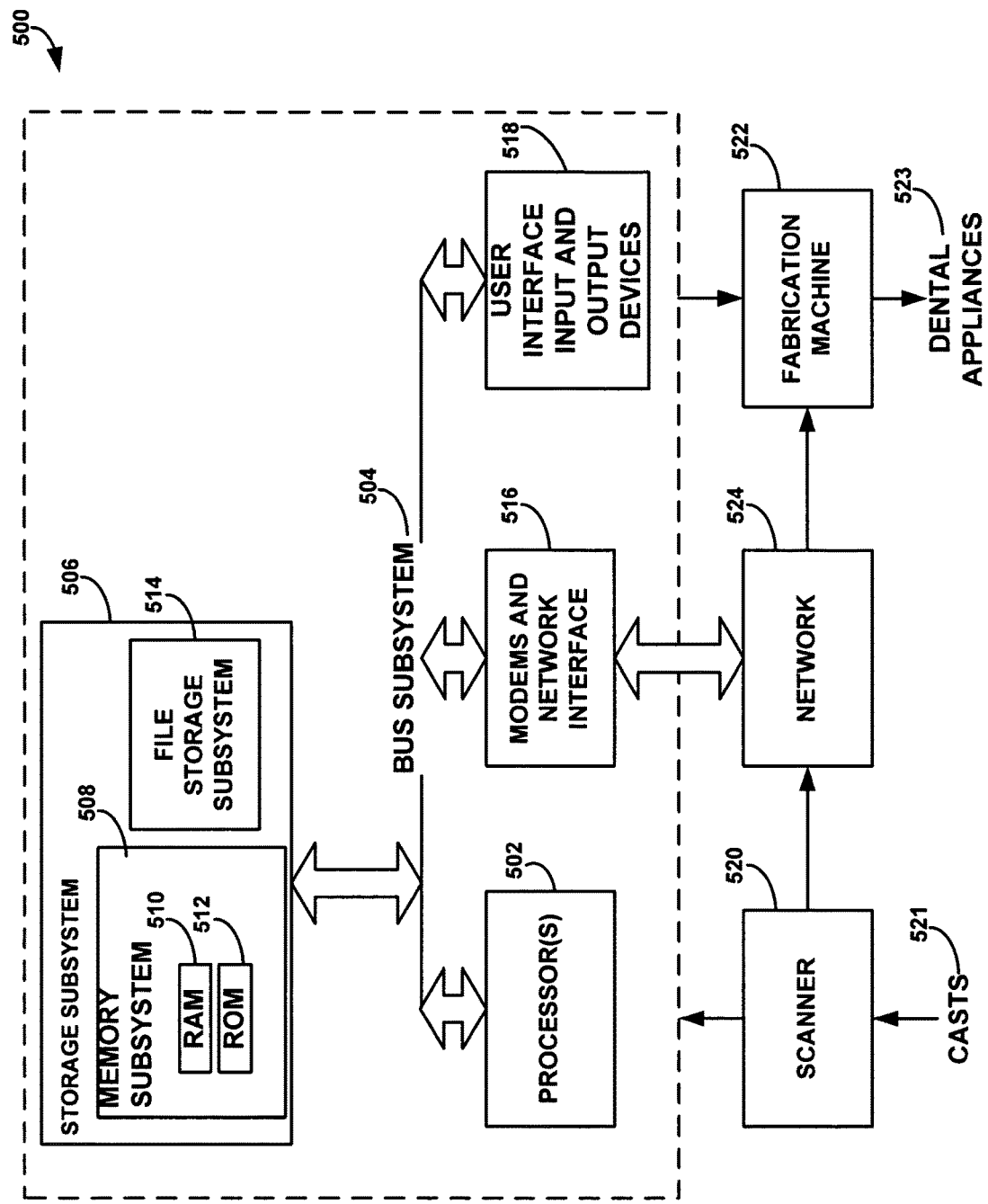
FIG. 9 is a diagram illustrating a computer system to support the fabrication of appliances.

FIG. 9 is a simplified block diagram of a data processing system 500 that may be used to develop orthodontic treatment plans. The data processing system 500 typically includes at least one processor 502 that communicates with a number of peripheral devices via bus subsystem 504. These peripheral devices typically include a storage subsystem 506 (including a memory subsystem 508 and a file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems via communication network interface 524. Data processing system 500 could be a terminal or a low-end personal computer or a high-end personal computer, workstation or mainframe.

The user interface input devices 518 typically include a keyboard and may further include a pointing device and a scanner. The pointing device may be an indirect pointing device such as a mouse, trackball, touchpad, or graphics tablet, or a direct pointing device such as a touch screen incorporated into the display, or a three dimensional pointing device, such as the gyroscopic pointing device described in U.S. Pat. No. 5,440,326. Other types of user interface input devices, such as voice recognition systems, can also be used. User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 506 maintains the basic required programming and data constructs. The program modules discussed above are typically stored in storage subsystem 506. As noted above, storage subsystem 506 typically comprises a memory subsystem 508 and a file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computer the ROM would include portions of the operating system; in the case of IBM-compatible personal computers, this would include the BIOS (basic input/output system).

File storage subsystem 514 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may be, for example, hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage sub-system could be connected via various local-area or wide-area network media, including telephone lines. Similarly, the input devices and display need not be at the same location as the processor, although it is anticipated that personal computers and workstations typically will be used.

Bus subsystem 504 is shown schematically as a single bus, but a typical system has a number of buses such as a local bus and one or more expansion buses (e.g., ADB, USB, SCSI, ISA, EISA, MCA, NuBus, or PCI), as well as serial and parallel ports. Network connections are usually established through a device such as a network adapter on one of these expansion buses or a modem on a serial port. The patient computer may be a desktop system or a portable system.

Scanner 520 is responsible for scanning casts 521 of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 via network interface 524.

Fabrication machine 522 fabricates dental appliances 523 based on intermediate and final data set information received from data processing system 500. In a distributed environment, fabrication machine 522 may be located at a remote location and receive data set information from data processing system 500 via network interface 524.

Figure 10:
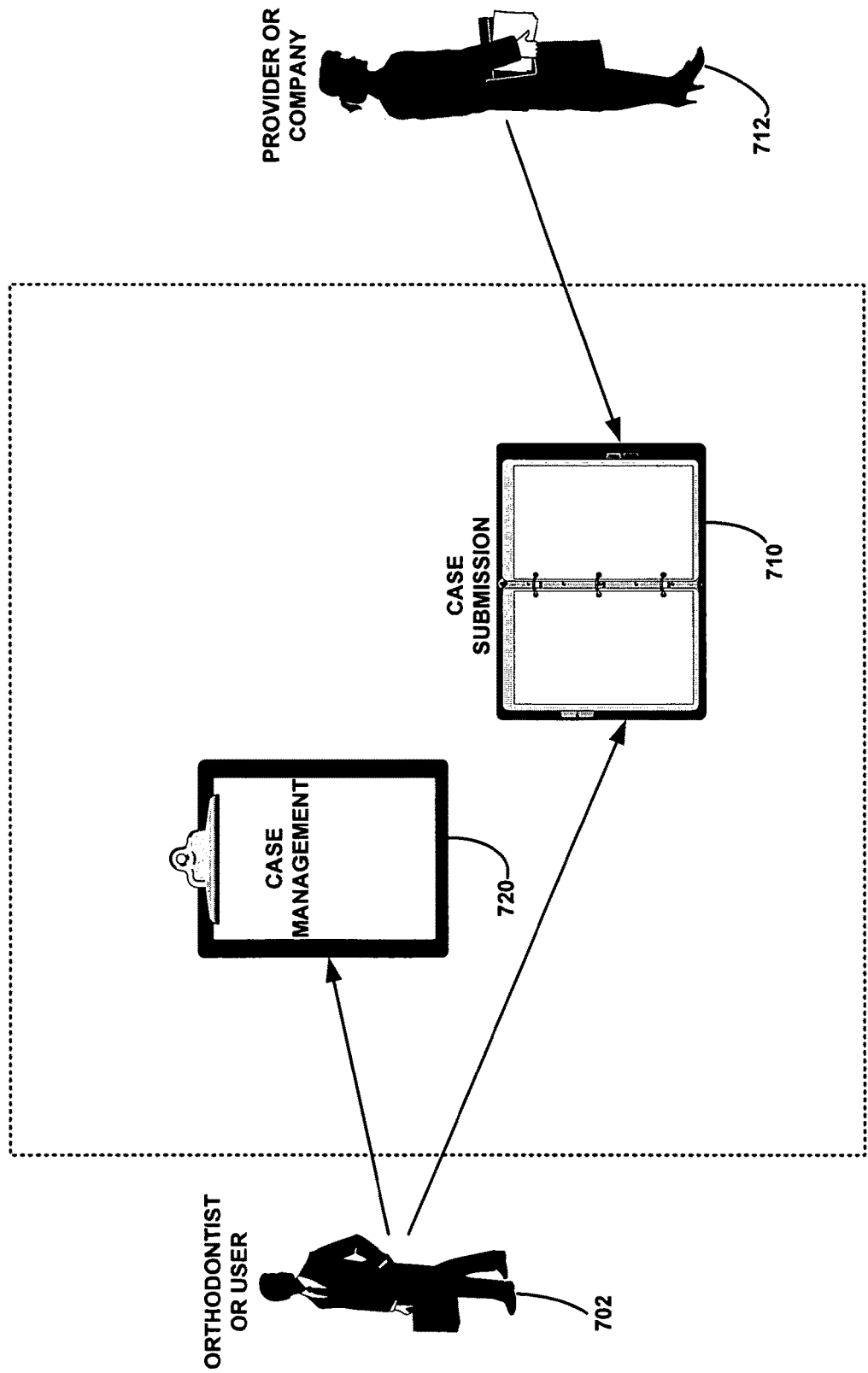
FIG. 10 is a diagram schematically showing information flow within and exterior of a network application according to an embodiment of the invention.

Referring now to FIG. 10, a virtual orthodontic practice system is shown. The system is a web-based transaction environment that allows qualified orthodontists and dental practitioners to submit malocclusion cases as candidates for treatment. The system is also used for managing the cases accepted for treatment. The treating professional can accomplish the case submission and case management process entirely within the web-based environment. As shown in FIG. 10, an orthodontist or treating professional 702 submits cases into a case submission system 710. The treating professional can also view and manage the case using a case management system 720. The case management system 720 also interacts with a provider 712, which operates the system of FIG. 8 in producing aligners for patients based on instructions from the treating professional 702.

Figure 11:
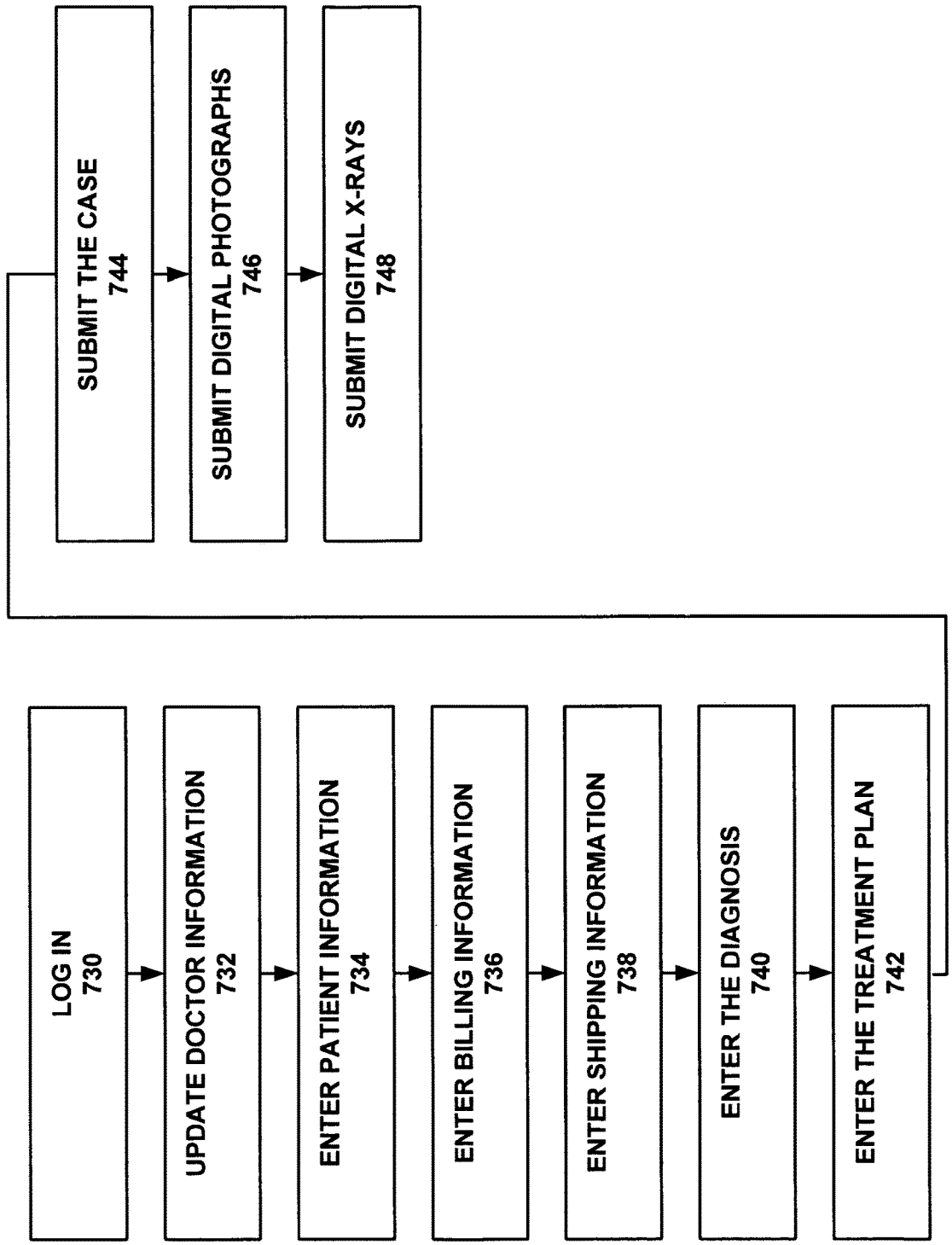
FIG. 11 is a flowchart showing a case submission scheme according to an embodiment of the invention.

FIG. 11 shows a process for submitting a new case. Case submission is the process of creating and submitting a malocclusion case as a candidate for the system's treatment, all within a web-based environment. First, the user clicks on a Start a New Case link to take the user to an On-line Treatment Planning Form where the user can complete the On-line Treatment Planning form and submit the form. The orthodontist or treatment professional initiates the case submission process by first logging in to the web application (step 730). The doctor information is updated (step 732). After a successful login, the treating professional can begin the case creation process. The treating professional enters the patient information (step 734), their practice information, the billing (step 736) and shipping (step 738) information, and finally the diagnosis (step 740) and treatment (step 742) plan. After the case details are finished, the treating professional submits the case information (step 744). Subsequently, the treating professional can submit the associated digital images (step 746) and x-rays (step 748). The submitted case is received by the provider 712. This completes the case submission process.

Once the user has submitted the On-line Treatment Planning Form, the user may print copies of the 'Treatment Planning Form Summary', save one copy for the user's records, and place the second copy in the Orthodontics Records box along with the same materials the user typically sends to the system. Next, the user prints a shipping label by clicking on the 'Print UPS Label' button that appears when the user submits a new case on-line. The shipping label is affixed to the outside of an orthodontics records box that contains a Treatment Planning Form Summary, a PVS impression of each arch in a separate foam bag, a bite registration in a separate foam bag, copies of the patient's x-rays, and copies of the patient's photos (intraoral and extraoral), for example.

Figure 12:
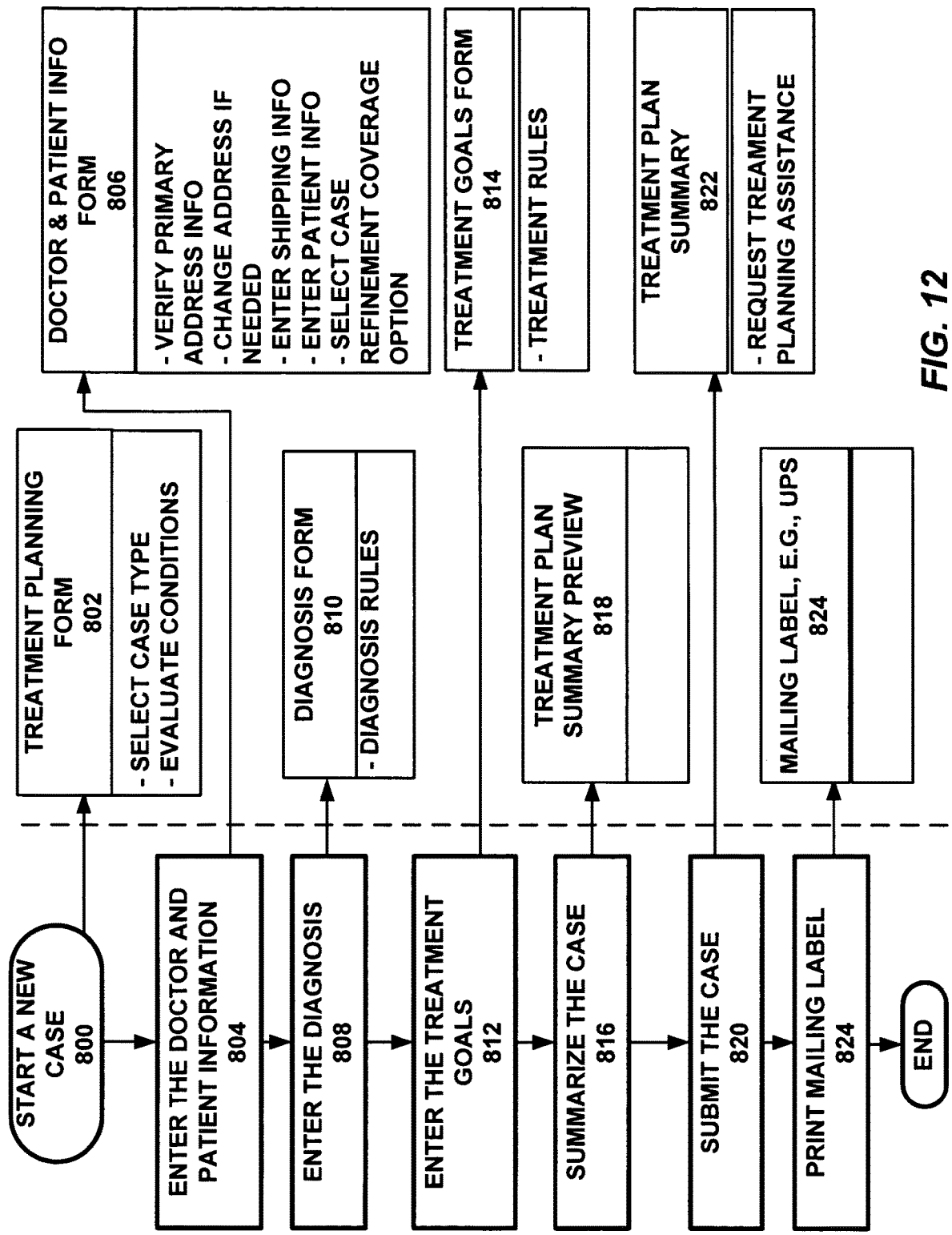
FIG. 12 is a flowchart showing a case management scheme according to an embodiment of the invention.

Referring now to the greater detail shown in FIG. 12, a website activity diagram for submitting a new case is detailed. First, a new case is started (step 800). This can be done using a treatment planning form (step 802). The treatment planning form allows the user to select a case type and to evaluate orthodontic conditions that may be encountered. From step 800, the process then captures doctor and patient information (step 804) using a doctor and patient information form (step 806). This form verifies address information and shipping information, patient information, and allows the doctor to enter or otherwise select case refinement coverage options, among others. From step 804, the doctor enters a diagnosis (step 808). This can be done through a diagnosis form (step 810). From step 808, the doctor then enters the treatment goals (step 812). This can be done using a treatment goals form (step 814). From step 812, the doctor then summarizes the case (step 816) using a treatment plan summary preview (step 818). From step 816, the case is submitted (step 820). This can be done using a treatment plan summary (step 822). From step 822, a shipping label is printed (step 824) using for example, a UPS label printing process (step 824) as described above for cases that are shipped using UPS.

Figure 13:
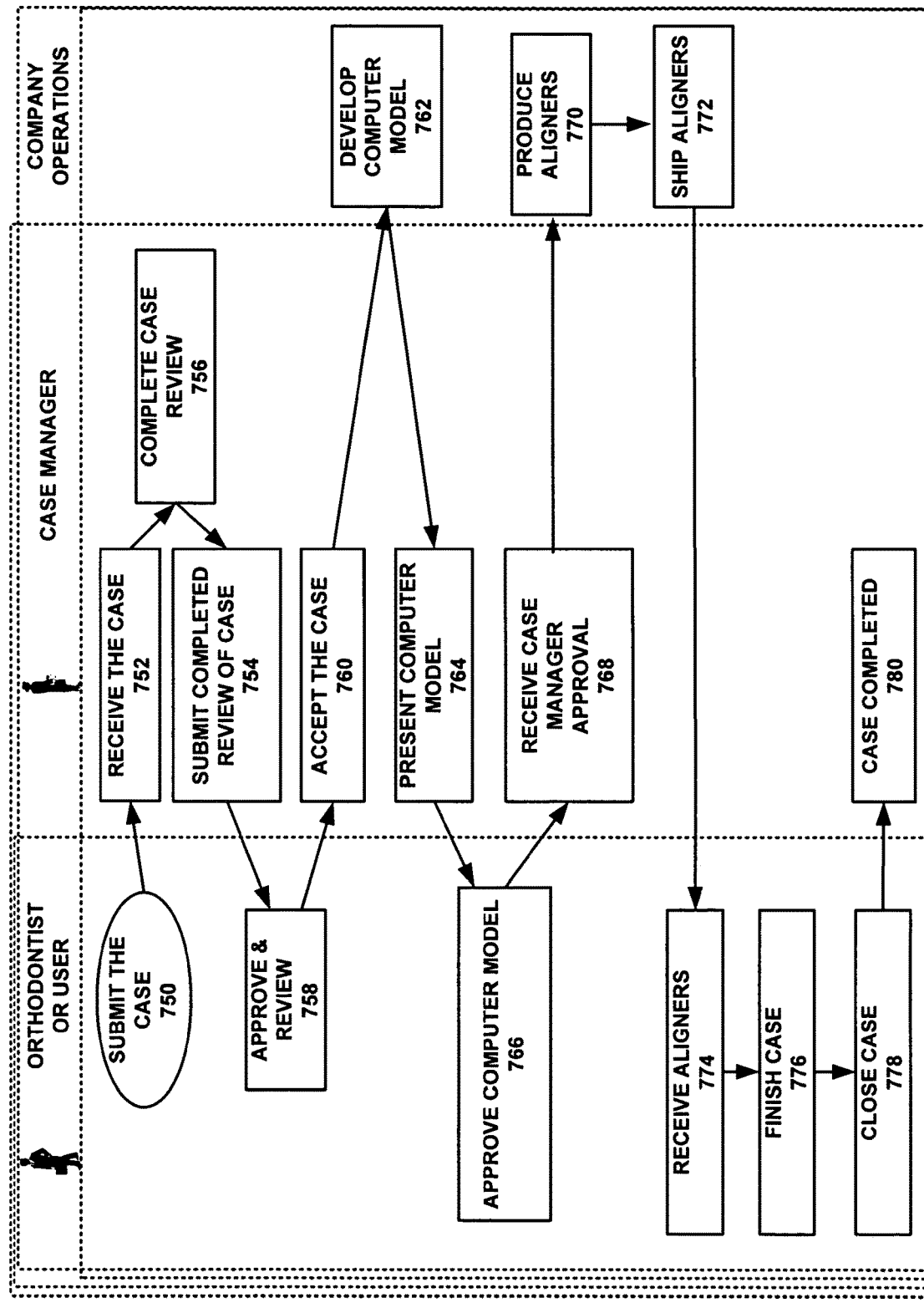
FIG. 13 shows a diagram illustrating potential activity on the website upon submission of a new case.

Turning now to FIG. 13, the case management process is detailed. Case management takes place after the treating professional has submitted the case, and includes the recursive review and approval process all taking place within the web environment. The case management process ends when the treating professional has finished and closed the case.

First, the treating professional submits the case (step 750) as, e.g., shown in FIGS. 11 and 12. The system receives the case over the network (step 752), and an experienced professional reviewer reviews the case (step 754). The completed review is submitted to the server (step 756) and the treating professional can review and approve the case (step 758). Upon receiving approval, the case manager accepts the case (step 760). The case is then forwarded to the system of FIG. 9 to develop a computer model (step 762). The computer model is then presented to the case manager (step 764), who in turn forwards the model to the treating professional for approval (step 766). The treating professional reviews and if he or she accepts the treatment plan, sends an approval to the case manager (step 768). The system of FIG. 9 then manufacturers the aligners (step 770). The produced aligners are then shipped (step 772) to the treating professional. Upon receipt of the fabricated aligners (step 774), the treating professional can finish the case (step 776). Upon conclusion of treatment, the case is closed (step 778) and the system of FIG. 9 sends an instruction to the case manager to close the case (step 780).

Figure 14:
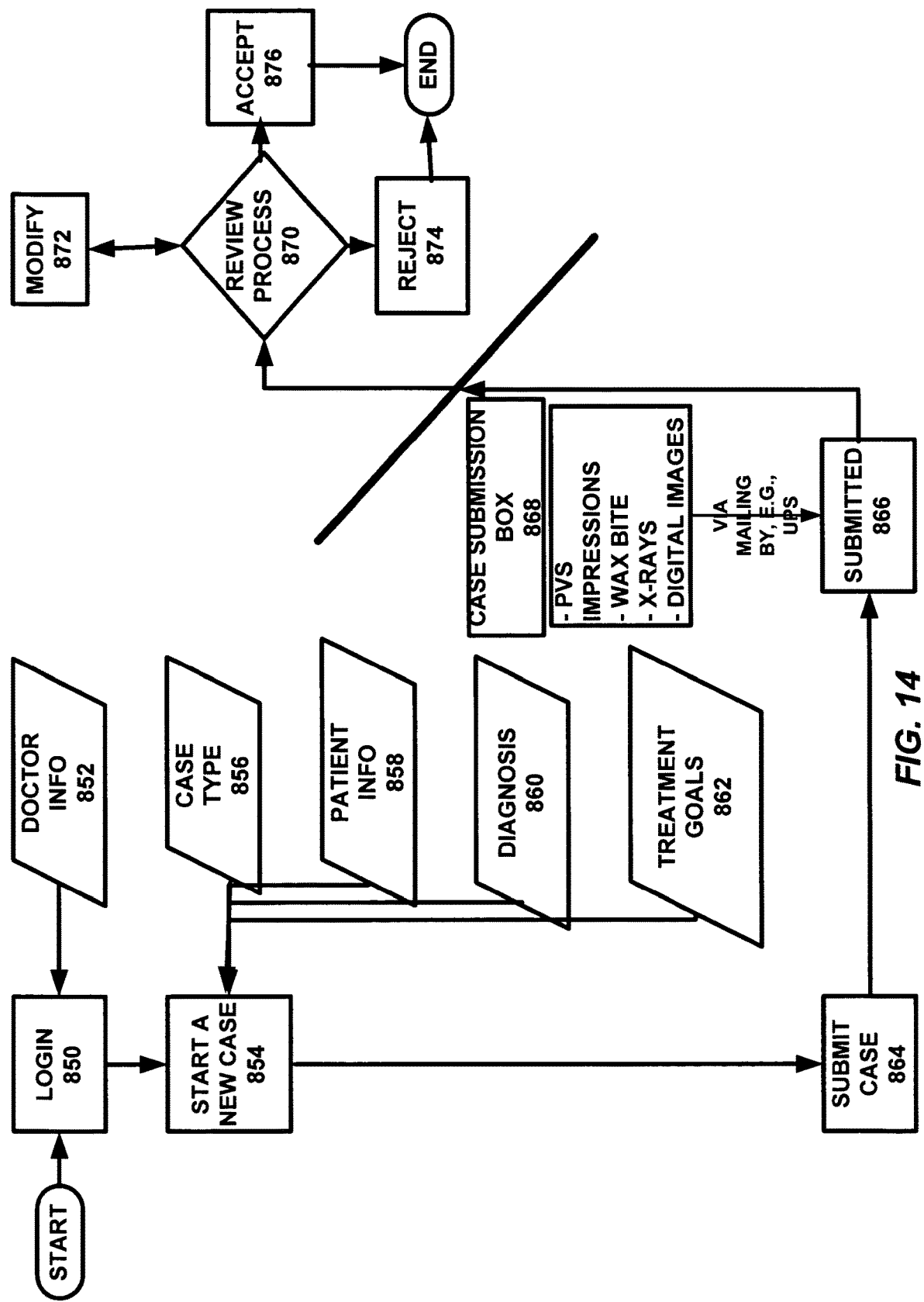
FIG. 14 is a flowchart illustrating another aspect of a new case submission, as well as a case review series of steps.

Referring now to FIG. 14, an online prescription workflow for new cases is shown. First, a user logs in (step 850). In this process, doctor information can be processed or input (step 852). Next, a new case can be started (step 854). In this step, case type information can be collected (step 856), patient information data can be collected (step 858), diagnosis information can be collected (step 860), or treatment goals can be collected (step 862). From step 854, the case can be submitted (step 864). This can be done over the network and a submission receipt can be delivered (step 866). Additional case submission information can also be submitted (step 868). This additional information may include PVS impressions, wax bites, x-rays, and digital images, among others. The information from the case submitted and the additional case submission data, if any, is then reviewed (step 870). The reviewer can modify (step 872), accept (step 876), or reject (step 874) the case.

Figure 15:
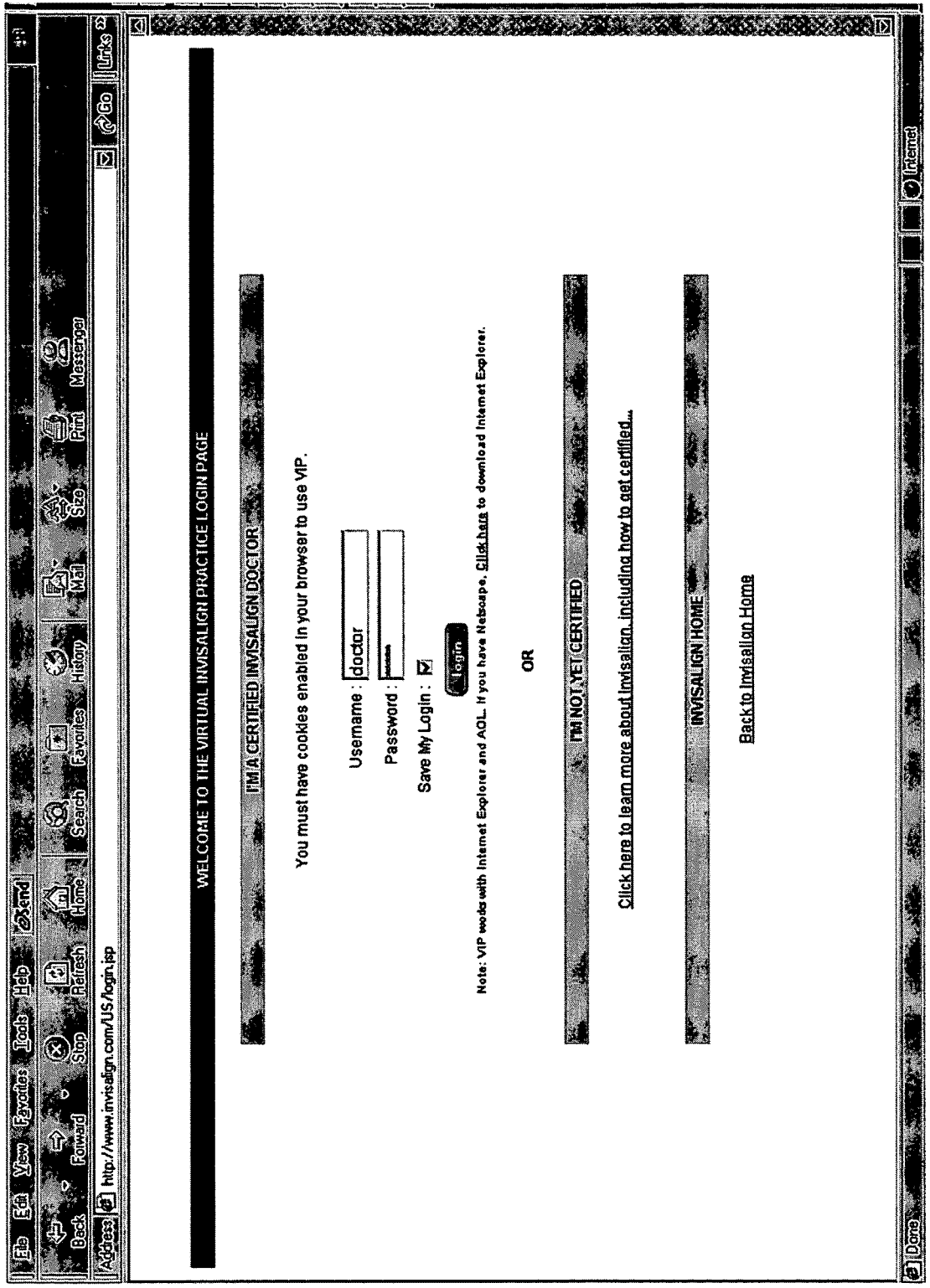
FIG. 15 is an exemplary home page of the web based interface.
Figure 16:
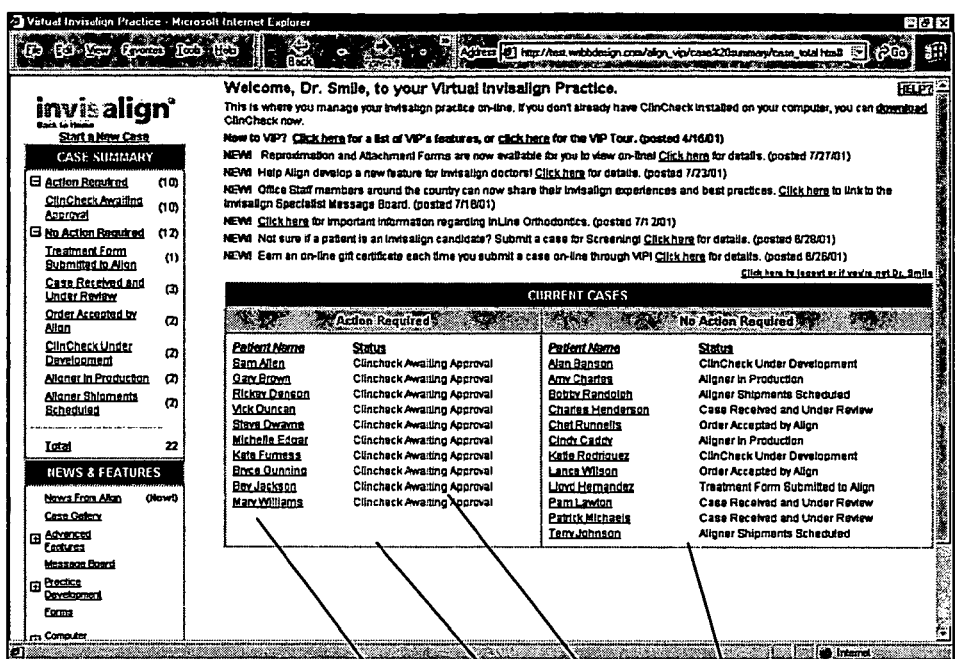
FIGS. 16-17 show exemplary treatment planning forms on a website according to an embodiment of the invention.
Figure 17:
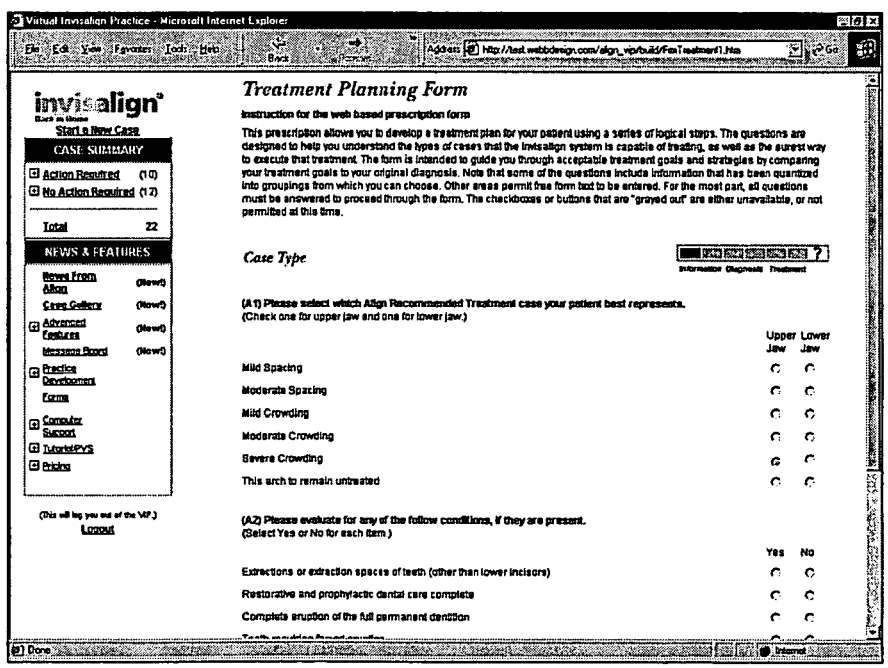

One web-based implementation of FIGS. 10-14 is discussed next. FIG. 15 shows an exemplary home page of the web-based interface. The web-based system of FIGS. 15-18B allows users such as doctors to manage the system practices on-line. The user can view all aspects of the patients' cases on-line. The user can also order advertising and marketing materials, chat on-line with other system doctors, review the system's how-to tutorials, and link to the user's personal website.

The web-based system helps users such as the treating doctors to ensure that appliances received from the provider 712 will treat the patient the way the user and provider intended. The system does this with a dynamic 3-D animation called a virtual treatment model. The system not only shows the user's patient's teeth going through their projected movement as a result of wearing the system appliances (aligners), but it also gives the user the ability to manipulate the model in time and space to ensure the treatment sequence is exactly what the user intended. The system gives the user control over the aligners the user will receive: if the animation the user sees does not depict the treatment or outcome the user intended, the system allows the user to send feedback to the provider 712 with instructions on how to re-set the case. After the provider 712 has received the user's explicit approval, the appliances are manufactured and sent to the user's office.

When the user views the case online through the provider 712's web site (for example, at www.invisalign.com), the system contacts the provider's computer system over the Internet and downloads the treatment model to the user's computer, e.g., at work or at home. The system then allows the user to play an animation showing the treatment progressing over time, starting and stopping at any point during the treatment. It also allows the user to inspect the treatment from any angle, or from as far away or as close as the user desires.

The system allows a treating professional, described below as a "user", to view the status of all the cases at any point in time. Within the home page 900, a Patient Chart appears on the right hand side of the page. The chart is divided into two columns—those cases that require action—Action Required 902—and those that do not—No Action Required 904. Within these lists, a status 908 will appear next to each patient's name 906. This status 908 identifies the current point of treatment for the patient 906. For example, if the user has patient John Doe in the Action Required column, and his status reads Awaiting Your Approval, the user will need to view and approve of an aspect of Mr. Doe's file in order to continue with his treatment.

Status categories that appear under Action Required can include the following:
Awaiting Approval
Treatment Form Waiting to be Submitted
Case Refinement Waiting to be Submitted
Screening Form Waiting to be Submitted
Case Screening Result is Ready
Case on Hold Awaiting New Impressions
Case Waiting to be Resumed by Doctor
Midcourse Correction Waiting to be Submitted
Further Materials Required
Status categories that can appear under No Action Required include the following:
Treatment Form Submitted to the Provider
Case Received and Under Review
Order Accepted by the Provider
Under Development
Shipments Scheduled
Aligners Shipped
Case Refinement Submitted
Case Currently Being Screened
Case Hold Requested by Doctor
Case Resume Requested by Doctor
Cancellation Requested by Doctor
Midcourse Correction Submitted
Certain status categories are now described in more detail.
Treatment Form Waiting to be Submitted This means that the user started a standard Online Treatment Planning Form for a patient, but did not submit it to the provider 712. The case will be stored under this category until submitting it.

Case Received and Under Review

Case Received and Under Review is a category of patients whose clinical items (Treatment Planning Forms, PVS impressions, Bite Registrations, X-rays, Photos) the provider 712 has received and is in the process of confirming that these patients are candidates for the system treatment. If the case is accepted for treatment, the status will change to Order Accepted by the provider 712. If the case is not accepted for treatment, the status will change to Order Not Accepted by the provider 712 and a representative will notify the user's office.

Order Accepted

Order Accepted is a category of patients whose cases have been accepted for treatment by the provider 712. The next status the user will see for this patient will be Under Development. When this patient's file has been developed, the status will then change status to Awaiting Approval. At that time, feedback to the system will be required in order to continue processing the case.

Under Development

Under Development is a category of patients whose files are currently being developed by the provider 712. As noted above, when the system is ready, the patient's status will change to Awaiting Approval. At that time, feedback to the system will be required in order to continue processing the case.

Awaiting Approval

Awaiting Approval is a category of patients whose files are ready for review and feedback. To review a patient's file, the user can click on the patient name in the home page. The user will be linked to the patient's Summary Page where the user, e.g., can view models. If the user accepts a patient's case, the status for the patient will change to The Aligner in Production. If the user requests modification of the file, the status will change back to Under Development.

Shipments Scheduled

Shipments Scheduled is a category of patients whose the aligners are currently being produced and are due to ship in the near term. To view a patient's scheduled ship date, the user can click on his or her name. The user will be linked to the patient's Summary Page where the user can view the ship date. Once the patient's aligners are shipped, the status will change to Aligners Shipped.

Aligners Shipped

Aligners Shipped is a category of patients whose aligners have already shipped. The user can check the date the aligners were shipped by clicking on the patient's name. The user will be linked to the patient's Summary Page where the user can view the ship date. This is the last status for a patient.

Case Refinement Waiting to be Submitted

Case Refinement Waiting to be Submitted is a category of patients whose Case Refinement Form the user started, but did not yet submit to the provider 712. To submit this form for a patient, the user can click on the patient's name. The user will be linked to the patient's Summary Page. From this page the user can continue filling out the form and submit it to the provider 712. Once the form is submitted, the status will change to Case Refinement Submitted.

Case Refinement Submitted

Case Refinement Submitted is a category of patients whose Case Refinement Form the user submitted to the provider 712. Once the provider 712 begins developing a new file for these patients, the patient status will change to Under Development. When the system is ready, the patient status will change to Awaiting Approval. At that time, feedback to the system will be required in order to continue processing the case.

Screening Form Waiting to be Submitted

Screening Form Waiting to be Submitted is a category of patients whose Screening Forms the user started, but did not submit to the provider 712. To submit this form for a patient, a user can click on the patient's name. The user will be linked to the patient's Summary Page. From this page the user can continue filling out the form and submit it to the provider 712. Once the form is submitted, the status will change to Case Currently Being Screened.

Case Currently Being Screened

Case Currently Being Screened is a category of patients whose Screening Forms the user submitted to the provider 712. These cases are currently being reviewed by the provider 712—when the review process is complete, the patient status will change to Case Screening Result is Ready.

Case Screening Result is Ready

Case Screening Result is Ready is a category of patients whose Screening Forms the user submitted to the provider 712 and whose results are ready for review. These cases are currently being reviewed by the provider 712—when the review process is complete, the patient status will change to Case Screening Result is Ready. After that status is achieved review the case screening results for a patient, the user can click on the patient's name.

Case on Hold Awaiting New Impressions

Case on Hold Awaiting New Impressions is a category of patients whose cases have been placed on hold by the provider 712 due to unusable PVS impressions. When the provider 712 places a case on hold, the user's office will be notified so that steps can be taken to resume the case as quickly as possible.

Case Waiting to be Resumed by Doctor

Case Waiting to be Resumed by Doctor is a category of patients whose cases the user has placed on hold—these cases will remain on hold until the user resumes them. To resume a case, the user can click on the patient's name. The user will be linked to the patient's Summary Page. From this page the user can click on the Resume This Case link.

Case Hold Requested by Doctor

Case Hold Requested by Doctor is a category of patients' whose cases the user has requested that the provider 712 place on hold. Before the provider 712 places the case on hold, the user will be called to confirm that the user wants the provider 712 to stop processing the case. Once the provider 712 has confirmed that the user wants the case placed on hold, the status will change to Case Waiting to be Resumed by Doctor. The user can then resume it by clicking on the patient's name. The user will be linked to the patient's Summary Page. From this page the user can click on the Resume This Case link.

Case Resume Requested by Doctor

Case Hold Requested by Doctor is a category of patients whose cases the user has requested that the provider 712 place on hold. Before the provider 712 places the case on hold, the user's office will be notified confirm that the user wants the provider 712 to stop processing the case. Once the provider 712 has confirmed that the user wants the case placed on hold, the status will change to Case Waiting to be Resumed by Doctor. The user can then resume it by clicking on the patient's name. The user will be linked to the patient's Summary Page. From this page the user can click on the Resume This Case link.

Cancellation Requested by Doctor

Cancellation Requested by Doctor is a category of patients whose cases the user has requested that the provider 712 cancel. Before the provider 712 cancels a case, the user's office will be called to confirm that the user wants the provider 712 to stop processing the case. Once the provider 712 has confirmed that the user wants the case cancelled, the case will be removed from the database.

Midcourse Correction Form Waiting to be Submitted

Midcourse Correction Form Waiting to be Submitted is a category of patients whose Midcourse Correction Forms the user started, but did not submit to the provider 712. To later submit this form for a patient, the user can click on the patient's name. The user will be linked to the patient's Summary Page. From this page the user can continue filling out the form and submit it to the provider 712. Once the form is submitted, the status will change to Midcourse Correction Submitted. Once the provider 712 has had a chance to review the user's request, the patient status will change to Under Development.

Midcourse Correction Submitted

Midcourse Correction Submitted is a category of patients' whose Midcourse Correction Forms the user recently submitted to the provider 712. Once the provider 712 has had a chance to review and process the request, the patient status will change to Under Development.

Further Materials Required

Further Materials Required is a category of patients whose files are incomplete and cannot be processed further until additional materials are sent to the provider 712. In most cases, this means that the Submission Box sent to the provider 712 did not include all necessary patient materials. When a case enters this status, the provider 712 will call the user's office to let the user know that further materials are required.

To view only certain cases, the user may click on the status category in the Case Summary box that the user is interested in viewing. For example, if the user would like to view only cases that are in the Awaiting Approval phase, the user clicks on that link. The patient chart on the right side of the page will now only display cases in the Awaiting Approval phase.

To return to a view of all the cases, the user clicks on Total to take the user back to the original patient chart. The user can also sort cases within any patient list by clicking on one of the column headings. For example, to sort cases by patient name, the user may click on the Patient Name heading. The cases will now be sorted in alphabetical order by patient name. The user can always identify how the patient list is sorted by noting which column heading is italicized.

Each of the patients in treatment has their own Patient Summary Page. The Patient Summary Page allows the user to view all aspects of a patient's case, from their file to their treatment history. To access a Patient's Summary Page, the user clicks on the name of the patient whose file the user would like to view. The user can find a list of all the patients on the Home Page. From the Patient Summary Page, the user can do each of the following:

View a Patient's Model
View Static Images
View Treatment History
View On-line Forms—Attachment and Reproximation
Create an Aligner Schedule
Place a Case on Hold
Cancel a Case One function supported by the system is to enable the user to complete an On-line Treatment Planning Form (see FIG. 16) quickly and efficiently.

On the Treatment Planning Form page the user can access the following:

On-line Treatment Planning Form
Paper Treatment Planning Form
Case Refinement Form
Mid-course Correction Form A template called Treatment Preferences can be used to allow the user to enter treatment information one time—this information is then incorporated into each form the user fills out, eliminating the need to enter redundant information each time the user submits a new case. The Treatment Preferences form will automatically appear in a separate window when the user clicks on the Start a New Case link for the first time. For each On-line Treatment Planning Form the user fills out, at the beginning of the form the user is given the option of activating the Treatment Preferences for that form. The user can change the Treatment Preferences at any time by clicking on the Treatment Preferences link that appears after the user has clicked on the Start a New Case link.

In this system, the form does not allow the user to advance to subsequent pages until the current page is completely filled out. In addition, the form has built-in logic; it does not permit the user to send in a form that has contradictory inputs, nor can the user submit a case that does not meet predetermined case selection criteria. These features greatly increase the likelihood that each submitted case would be accepted for treatment. If the user requires assistance in filling out the form, the user clicks on the question mark symbol within the form to view the comprehensive Help section.

Yet another feature is a Case Selection Expansion option. Case Selection Expansion allows doctors experienced in the system to submit cases beyond the limits of what is normally accepted through the On-line Treatment Planning Form. If the user is an experienced user who has submitted a large number of cases, the user is eligible for Case Selection Expansion. Once classified as an experienced user, the user will see a screen asking whether the user would like to use the standard On-line Treatment Planning Form or the Case Selection Expansion Form, which allows more flexibility. If the user selects the Case Selection Expansion Form, the user is prompted to sign a waiver. Besides relaxed case selection criteria for the Case Selection Expansion Form, the user will find the two submission forms are identical.

Yet another feature in this embodiment is case screening. If the user is not sure whether a case is appropriate for system treatment and would like feedback from the system, the user can use the Case Screening feature. The user must be able to submit digital photos on-line to use this feature. In one embodiment, to screen a new case, the user clicks on a Case Screening link, enters the office information and the patient's information, enters the treatment plan and goals for the patient, and uploads digital photos of the case—either individual photos or a composite photo. After submission, a professional reviewer, at the provider end, reviews and provides comments and/or suggestions for treatment. If a patient's screening result is ready, that patient's status is listed as Case Screening Result is Ready. The user can then click on the patient's name to view the screening result and to submit the case for treatment.

The system can also handle case refinement situations. Case refinement occurs when additional aligners beyond the last stage are needed to move a patient's teeth closer to the desired final outcome approved by the user in the system. If the user has a case that qualifies for Case Refinement, the user's next step is to submit a Case Refinement Form for that case. Once the user has submitted a Case Refinement Form, the user can track the status of the form through the Home Page shown in FIG. 15. When the form is submitted, the patient's status will change to Case Refinement Submitted. When a new file begins production, the status will change to Under Development. Once the file is ready for review, the status will change again to Awaiting Approval.

In instances where clinical results deviate from the original treatment plan such that the aligner(s) no longer fit, a Mid-Course Correction is necessary. This may be due to any or a combination of the following:

Patient underwent dental work during the course of treatment
Poor patient compliance
Treatment goal has changed
Case has deviated from the approved course of treatment If the user has a case that qualifies for Mid-Course Correction, the next step is to submit a Mid-Course Correction Form for that case. Once the user has submitted a Mid-Course Correction Form, the user can track the status of the form through the Home Page. When the form is submitted, the patient's status will change to Mid-Course Correction Form Submitted. When a new file begins production, the status will change to Under Development. Unlike Case Refinement Cases, Mid-Course Correction files do not require feedback. Once the file is ready, the status will change again to Aligner Shipments Scheduled.

Figure 18A:
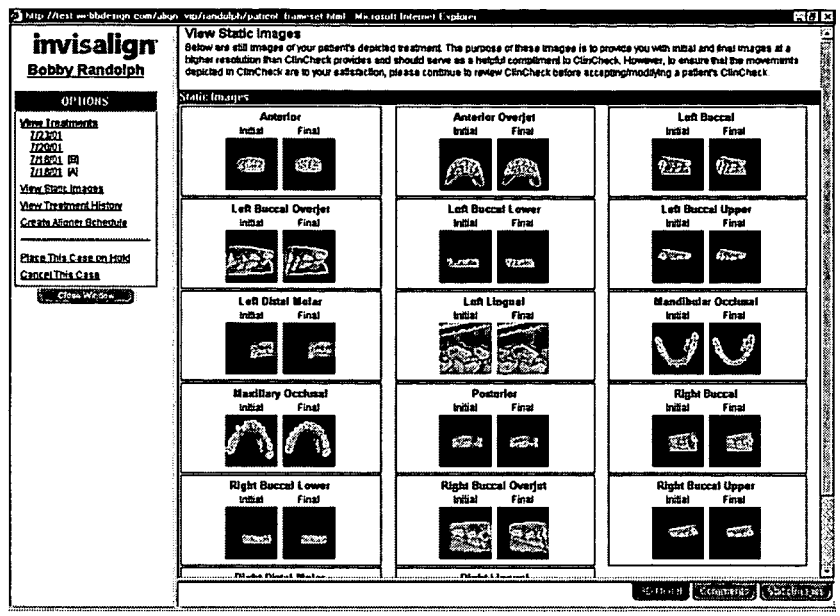
FIG. 18A shows a web page depicting static image displays, "before" and "after", of various views of a patient's gums and teeth.
Figure 18B:
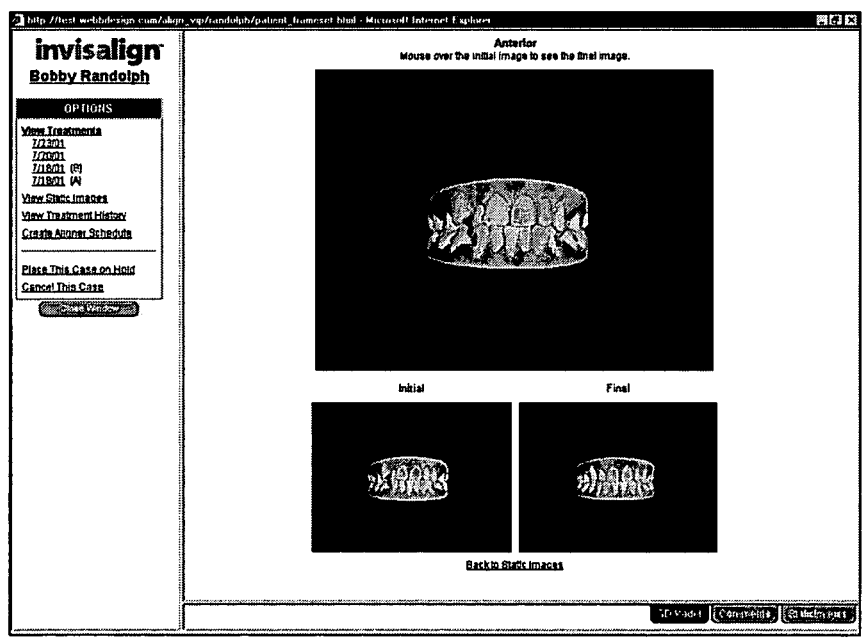
FIG. 18B shows a more detailed view of a static image from FIG. 18A.

FIGS. 18A and 18B show exemplary views of static images of a patient's teeth. The benefit of the static images is that they provide the user with initial and final images of the depicted treatment at a high resolution. To view a patient's static images, the user can click on the View Static Images link within the Options menu bar on the left side of a Patient's Summary Page. Alternatively, the user can access static images by clicking on the Static Images link at the bottom of a Patient's Summary Page. Once viewing the images, the user can enlarge them for a better view by clicking on them. The user can scroll the mouse over the image to view the initial and final views of the patient's depicted treatment. The bottom images provide a side-by-side comparison of the initial and final views.

The system can also allow the user to view a patient's dental model. To view a patient's file, the user clicks on the name of the patient whose file the user would like to view. The user can use the system to see many different views of a treatment model. The user can zoom in and out, hide the upper and lower arches, and rotate the model to allow viewing from different angles. The user can choose to see the model, in one embodiment, from fourteen different pre-set angles. The user can rotate a model to any angle, making it seem to spin in the window. The user can position the mouse inside the model window and click and hold the left mouse button while dragging the mouse in the direction that the user wants to move the model. The model rotates as the user moves the mouse. As an example, the user can start with the right buccal view of the model. The user must click and hold the left mouse button and drag the mouse from right to left. As the user does so, the model rotates so the user can see all of the teeth as the model moves.

If the user would like to take a closer look at a model, the user can zoom in. Conversely, if the user would like to see a view of the model from further away, the user can zoom out. To zoom, the user may press and hold the Control (Ctrl) key. Positioning the mouse inside the model window, the user may click and hold the left mouse button and drag the mouse up to zoom out and down to zoom in. The further the user drags, the further the user will zoom. Alternatively, if the mouse has a mouse wheel, the user can turn the mouse wheel to zoom in and out. The user can also slide the model up and down, and left and right. To slide the model, the user may, e.g., press and hold the Shift key, then click and drag the mouse. The model consequently moves in the direction of the mouse motion. This motion can be useful when the user has a zoomed-in view of the model, and the user wishes to view another part of the model. The user can hide the upper or lower arch to see an unobstructed view of the other arch. This is useful, for example, when looking at the occlusal surface of either arch. To hide the upper arch, the user may click the checked box next to Show Upper Jaw in the left menu bar. The check mark is then removed and the upper arch disappears from view. To hide the lower arch, the user may click the checked box next to Show Lower Jaw in the Dialog box. The check mark is then removed and the lower arch disappears from view. When the user hides either arch, the user can still rotate the model so the user can see it from various angles. Once the user has hidden an arch, the user can show it again. To show an arch once the user has hidden it, the user must re-select the Show Upper Jaw or Show Lower Jaw check box from the left bar menu. When the boxes show check marks, the arches are shown. The user can also select the level of detail of the model. On the left menu bar, the options Show Low Resolution and Show High Resolution appear. By default, Show Low Resolution is selected. Alternatively, the user can select Show High Resolution to show a more detailed version of the model. To print a model in its current view, the user may click the Print icon or right-click the mouse over the window and select Print from the right mouse button menu. The animation allows the user to see how a patient is projected to progress using the system. Using the animation controls located in the lower right corner of the model window, the user can play, stop, rewind and fast-forward the animation. The user can also step forward or backward through the animation stage by stage (e.g., where a stage corresponds to one set of aligners). To play an animation, the user clicks the Play button. The Play button then becomes the Stop button. To stop an animation, the user clicks the Stop button. To resume playing the animation, the Play button is clicked. When the user rewinds an animation, the model returns to its beginning position. To rewind an animation, the user can click the Rewind (<<) button. To rewind the model stage-by-stage, the user can click the Back (<) button and the model will rewind one stage. When the user fast-forwards an animation, the model advances to its final position. To fast-forward an animation, the user can click the Fast Forward (>>) button. To view the model stage-by-stage, the user can click the Forward (>) button and the model will advance one stage.

Other features supported by the web-based system of FIG. 10 includes Viewing Current/Archived News; Viewing the Case Gallery where the user can view before and after pictures of past system patients by visiting the system Case Gallery; Downloading All Files at Once, where the user can view the patients' cases without being connected to the Internet by downloading a series of patient files; Printing a List of All Patients; and a Message Board, where the users talk with other system doctors to share experiences with the product so the user can learn from and offer suggestions to other doctors who are using the provider 712.

Figure 19:
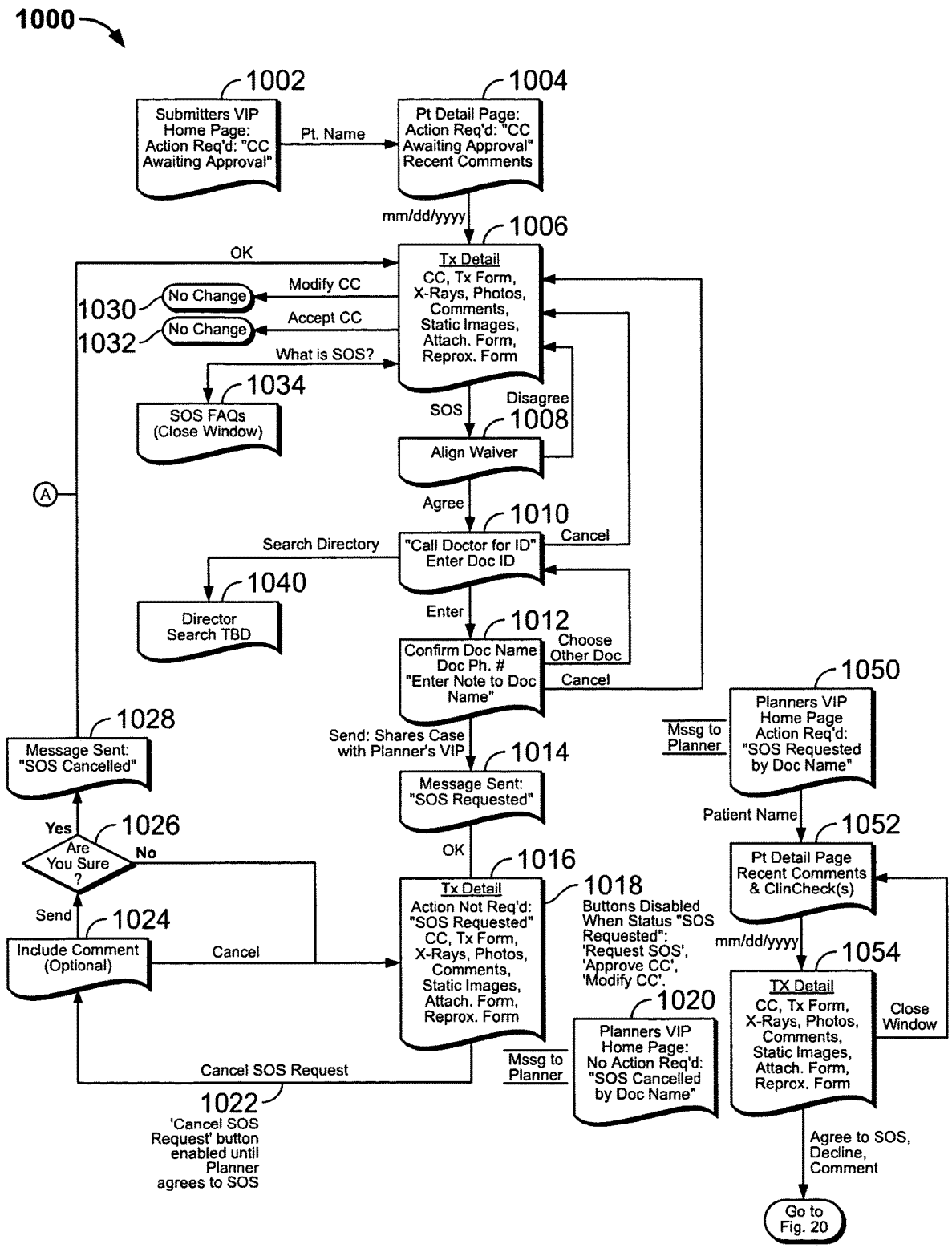
FIGS. 19-23 show an embodiment of a second opinion service (SOS) that provides an opportunity for inexperienced professionals to receive advice from experienced professionals in treating patients.

FIGS. 19-23 show one embodiment of a second opinion service (SOS) that provides an opportunity for inexperienced professionals to receive advice from experienced professionals in treating their patients. Referring now to FIG. 19, a second opinion service process 1000 is started when a doctor submitter receives notice on his or her web page that a clinical check (CC) file is present and awaits approval (1002). The CC file specifies teeth movement in each treatment stage, where each stage causes teeth to be incrementally moved. The CC file allows the doctor to visualize the treatment plan, including the teeth position at each stage. In one embodiment, the doctor sends a prescription to a provider/company 712 (FIG. 10). One such provider/company 712 is Align Technology, Inc. in Santa Clara, Calif. The provider 712 generates a CC file and allows the doctor to review and approve the CC file over the Internet in this embodiment. In one embodiment, a web-based system called Virtual Invisalign Practice (VIP) available from Align Technology is used to securely communicate patient information over the Web.

In 1004, the doctor is given an opportunity to view the proposed CC file (from provider 712) and comments are either entered by him or by the provider/company 712. The doctor can view files and other materials previously submitted such as x-rays, photographs or comments (1006). From 1006, the doctor has the opportunity to request a SOS by clicking a button, for example, the doctor is shown an agreement form such as a waiver form (1008). In one embodiment, the form describes each party's responsibilities with respect to the SOS process. If the doctor agrees, the doctor can proceed. Alternatively, if the doctor disagrees, the process loops back to 1006. The doctor can also modify or accept the ClinCheck file, in which case no change is noted in 1030-1032. Also, the doctor can check on "what is SOS," and a frequently asked question (FAQ) page is displayed at 1034.

In 1010-1012, if the doctor accepts the agreement, the doctor enters a doctor identification of a consulting doctor or planning doctor who plans or revises the treatment plan for the requesting doctor. The system can perform a directory search at 1040. The system shows the consulting doctor's contact information and gives the requesting doctor an opportunity to confirm. Once the doctor verifies that there is no typographical error the doctor can enter comments and send a message to the planning doctor to request SOS assistance at 1014. At 1014, once the message has been sent, the consulting doctor sees a status of "SOS Requested" on his home page. At 1016, the information sent includes ClinCheck form, prescription data, and supporting data such as X-rays, photos, comments, static images, attachment forms and reproximation forms. Next, buttons are disabled when the case status involves SOS Request, Approve ClinCheck, and Modify ClinCheck, among others (1018). At 1020-1024, after the SOS has been requested, the requesting doctor can cancel the request before the planning doctor has accepted the SOS. Upon requesting a cancellation, the doctor has an option to include additional comments. At 1026, if a cancellation occurs, a confirmation is generated to update the patient status on the doctor's home page to indicate "SOS Cancelled" (1028).

At 1050, upon submission of the SOS by the submitting doctor, the planning doctor's home page will show a new patient with status of "SOS Requested by Doc Name." At 1052, the patient detail page shows recent comments and CC information. At 1054, when the doctor clicks on the patient detail page, the doctor also views all other details and information that the submitting doctor has.

Figure 20:
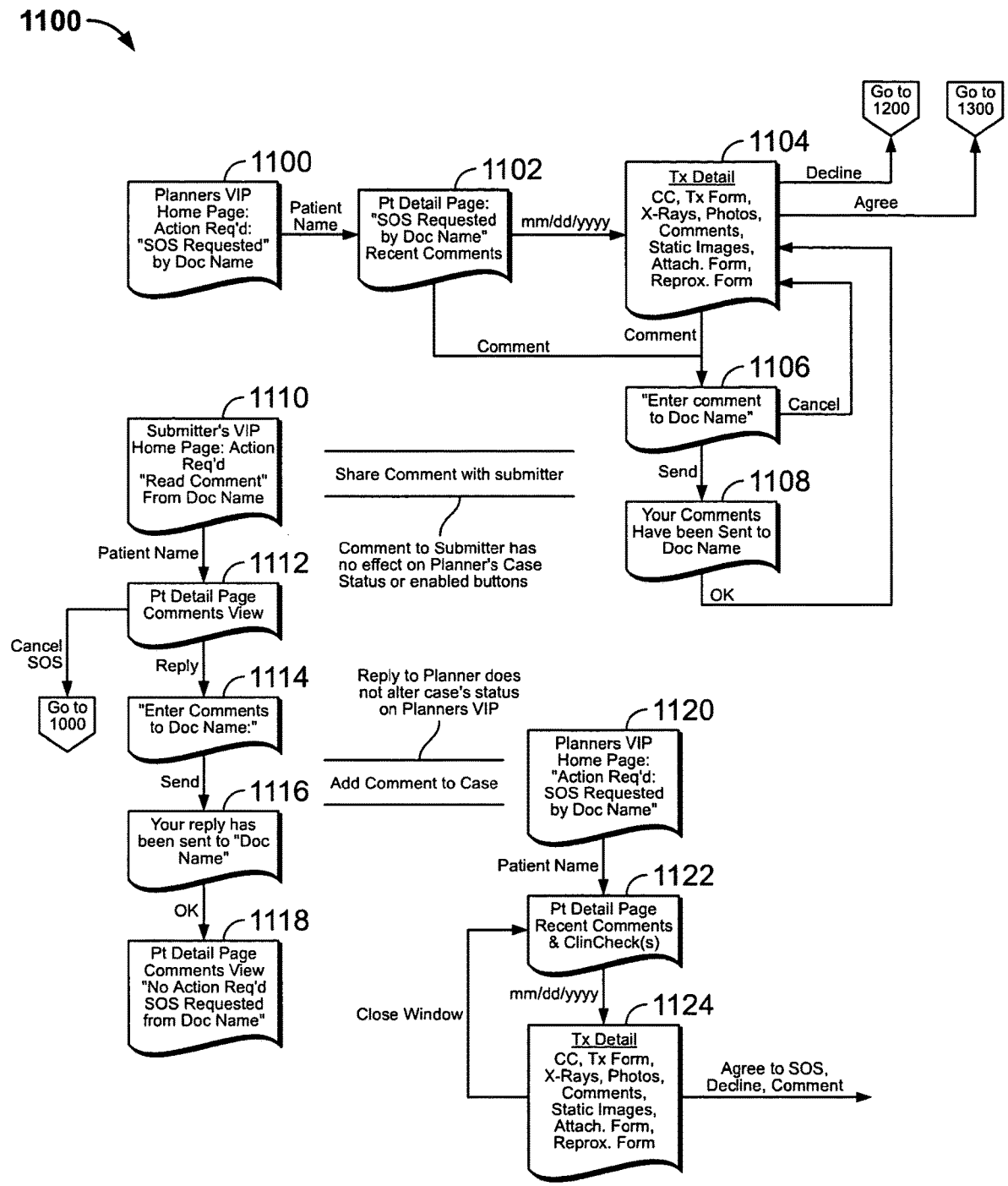

Turning now to FIG. 20, at 1100, the planning doctor's home page shows an action item "SOS requested" by the requesting doctor's name. The patient detail page is updated with the SOS Requested by Doctor Name (1102). At 1104, the doctor can click on the patient detail and review information from the submitting doctor. At 1108, the comment to the doctor is captured (1106), and upon transmission, the system updates the status as Comments Have Been Sent (1108).

The planning/consulting doctor can look at the CC file and decide if the doctor wishes to accept the case. If the doctor wants to decline the case, the doctor can enter a comment and send to the requesting doctor. Otherwise, the doctor can choose whether the doctor wants to decline or agree, as shown in more details in FIGS. 21-22.

At 1110, when the planning doctor submits a comment to the submitting doctor the submitting doctor will see a status item on his home page as "Read comment" from the planning doctor. The doctor clicks on the patient name and the doctor proceeds to 1112 where the doctor can review a particular patient's detail page and the case comments. At 1114, if the doctor chooses to reply the doctor can click on reply to enter comments to the planning doctor. At 1116, when the requesting doctor clicks the send button, a notification will be provided to provide feedback that a reply has been sent to the planning doctor. At 1118, the doctor is taken to the patient's detail page indicating "No action required—SOS requested from doctor name." At 1120, when the doctor adds a comment the planning doctor will then see a status change on his web page stating that "Action is required SOS requested by doctor's name". At 1122, when the doctor clicks on the patient's name the doctor is taken to the patient's detail page, and at 1124, the doctor can review the patient's detailed information, as previously discussed.

Figure 21:
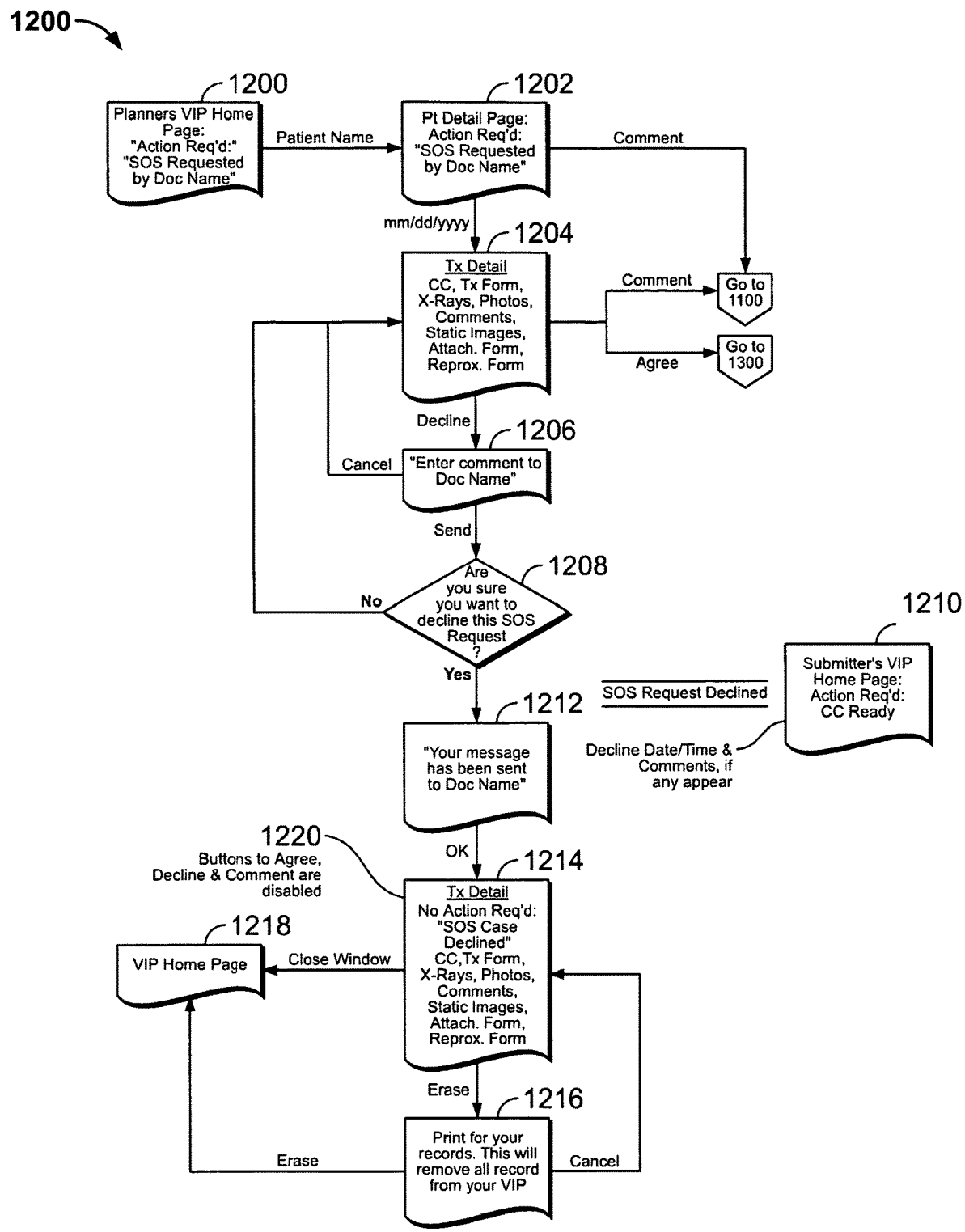

Turning now to FIG. 21, at 1200—Planners VIP has the patient name listed under "Action required" where status is "SOS Requested." At 1202, the patient detail page is updated with the Action "SOS Requested by Doctor Name." At 1204, the doctor reviews the information and has the option to accept or decline the case. If the doctor accepts the case, the process jumps to 1300 and if not, the process proceeds to 1206, where the doctor sends a cancellation request to the submitting doctor. At 1208, the doctor can change his/her decision. In this case, the SOS Request is declined and the submitter's page is updated with the status that "ClinCheck Ready" at 1210. At 1212, if the doctor wants to continue with SOS, the process shows the doctor a confirmation that his/her message has been sent and the SOS request has been declined. At 1214, the doctor is shown the patient detail page where the doctor views the patient's information. The buttons to Agree, Decline and Comment are disabled at 1220.

At 1216, the doctor has the option to erase all information relating to a patient's case so that the doctor will no longer have a record of the patient on his web page. From either 1214 or 1216, the home page can be accessed at 1218.

Figure 22:
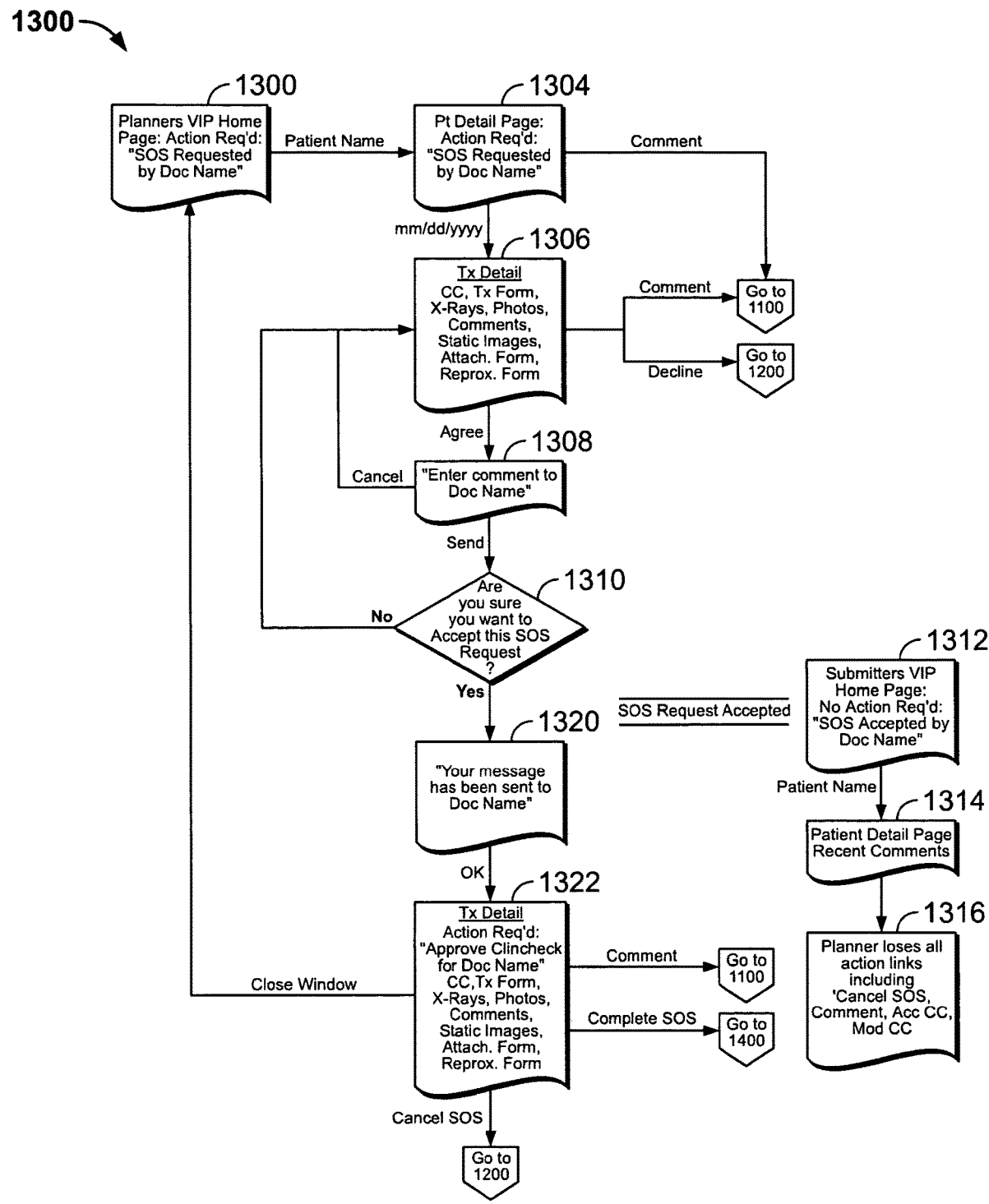

Turning now to FIG. 22, at 1304, doctor has accepted the SOS case and the patient name is displayed on the web page and the doctor can click on the patient's name to review the case information. At 1306, the treatment detail is communicated. At 1308, the planning doctor can communicate with the submitting doctor through comments. If the doctor chooses to comment, the process jumps to 1100. If the doctor chooses to decline, the process proceeds to 1200. At 1310, the doctor can accept the SOS request and at 1320, once the doctor has accepted the SOS, a confirmation is sent to both himself and to the submitting doctor. If the SOS Request is accepted, the submitter's home page is updated in 1312 and the patient detail page is updated in 1314. At 1316, the links such as Cancel SOS, Comment, among others are disabled.

The treatment prescription is updated at 1322, and the process can update the VIP home page with action required as "SOS Requested by Doctor Name" at 1300.

Figure 23:
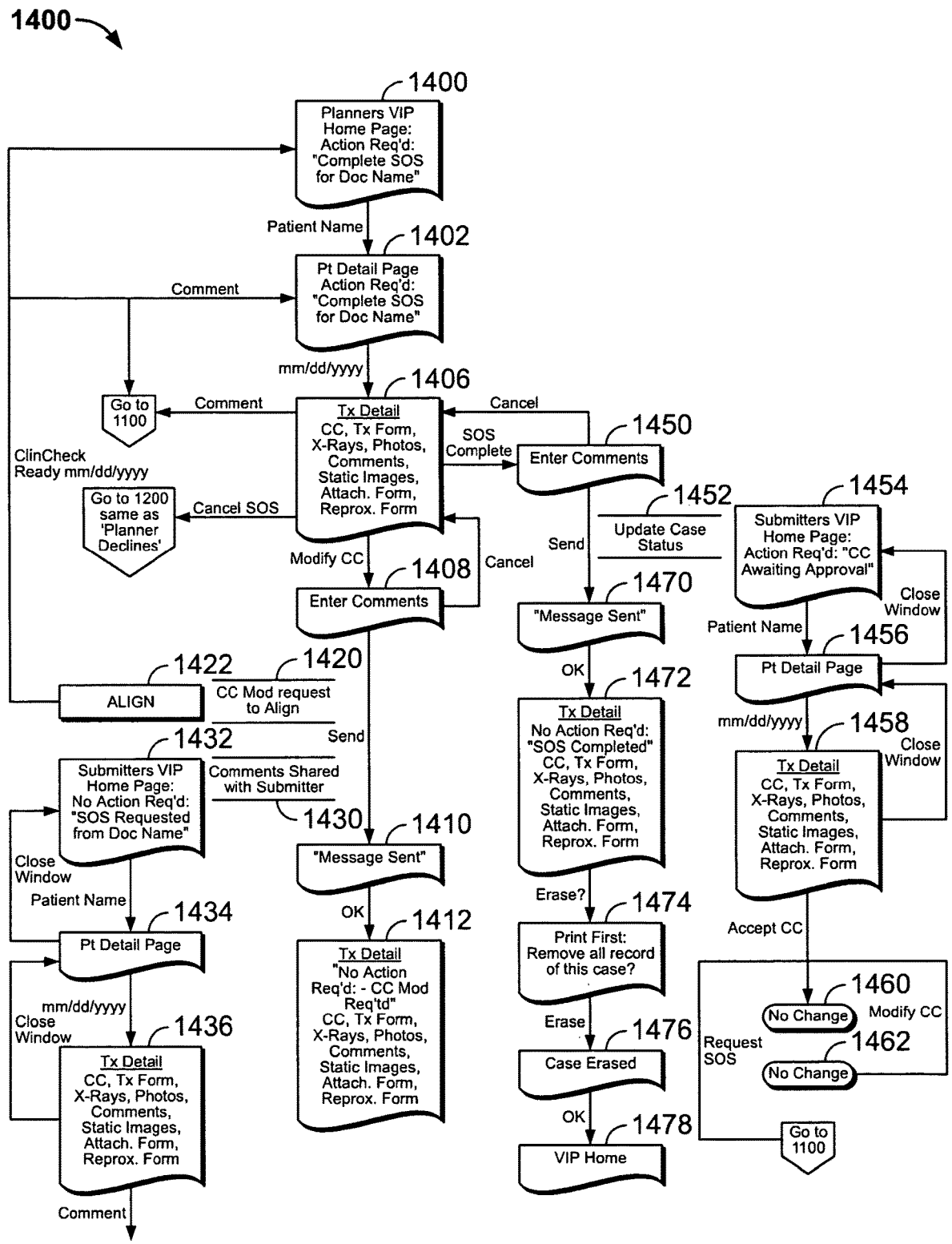

Once the doctor has accepted the SOS the doctor has the option to modify the CC data as previously mentioned, which proceeds to FIG. 23, or at any point during the SOS process the doctor has the option to cancel SOS and go to 1100 or to 1200 as displayed on FIG. 22. The doctor sees all the information available to the submitting doctor. The planning doctor then has an option to request modification of the ClinCheck (CC) file. The doctor can also enter comments and request certain modifications and the information is sent to the company/provider such as Align Technology on behalf of the submitting doctor. If the doctor agrees, the doctor can enter a comment to the submitting doctor.

Referring now to FIG. 23, at 1400, the doctor can see the patient name on the home page with action required "Complete SOS for doctor name". When the doctor clicks on the patient's name the doctor views all the same information the submitting doctor has in his patient summary page at 1402. At 1406-1408, the doctor can review the same information available to the submitting doctor. At this point, the doctor can cancel SOS (go to 1200), or the doctor can submit a comment to the submitting doctor (go to 1100).

From 1408, the ClinCheck modification request is sent to the dental supplier such as Align Technology, Inc., at 1420. Upon receipt by the supplier at 1422, the process notes that the CC file is ready and loops to 1400.

If comments are to be shared with the submitter at 1430, the submitter's home page is updated at 1432 and the patient detail page is updated at 1434. Also, the treatment detail page is updated at 1436.

Alternatively, the doctor can request to modify CC data, or the doctor can enter comments to the company provider at 1410. If so, notification is then provided to him that the comment has been sent successfully to the company. At 1412, once the doctor submits a comment to the company to request CC modification, the doctor's VIP page is updated to show that No Action Required—"CC Modification Requested". At 1450, when the planning doctor accepts the modified clinical check file, the doctor can click on an SOS complete button, at that point the doctor has the option to enter additional comments that the doctor can then submit to the submitting doctor. The case status is updated at 1452. At 1470, the doctor then gets a confirmation. At 1472, the doctor has the option to erase all patient information from his system upon completion of the case. If he selects this option, at 1474, the doctor is prompted to print out information on the case to be removed. At 1476, upon erasure, a notification will be provided that the case has been erased. At 1478, when the doctor clicks on an OK button, the doctor is returned to the VIP homepage.

At 1454, once the SOS work has been completed by the planning doctor, the submitting doctor is notified that an updated CC file awaits approval on his VIP homepage. At that point the doctor can then click on the patient name. At 1456, the doctor can see the patient detail information. At 1458, the doctor can click on the updated CC file and view the modifications requested by the planning doctor. At 1460, the doctor can accept the CC file if the doctor approves of the proposed changes. If not, at 1462, the doctor can request another modification of the CC file. Alternatively, the doctor can request a second SOS to the same planning doctor or a different planning doctor. If so, the process loops to 1000.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly.

What is claimed is:

1. A virtual health-care system for improved generation of digital models for fabricating orthodontic appliances by a fabrication machine, comprising:
   a fabrication machine configured to fabricate one or more orthodontic appliances for repositioning a patient's teeth; and
   a server comprising storage media having instructions that when executed cause the server to:
      generate treatment visualization data representing an orthodontic treatment plan for the patient's teeth, wherein the treatment visualization data is stored in a file storage subsystem associated with the server, wherein the treatment visualization data is based at least in part on data received from a dental scanner, and wherein the treatment visualization data comprises one or more manipulable 3-D models of the patient's teeth, wherein the one or more manipulable 3-D models are: (1) configured to be displayed in a web browser via a viewer plug-in module as an animated display of the patient's teeth moving through three or more successive arrangements, and (2) configured to allow a user to modify a position of at least one tooth of the one or more manipulable 3-D models by clicking on the at least one tooth in the web browser via the viewer plug-in module using a pointing device;
      transmit the treatment visualization data to a treating professional computer or a patient computer prior to adjustment of the patient's teeth according to the treatment plan;
      receive modified treatment visualization data, wherein the modified treatment visualization data comprises a modified tooth position of at least one tooth of the one or more manipulable 3-D models made in the web browser via the viewer plug-in module by a user clicking on the at least one tooth using a pointing device;
      modify the orthodontic treatment plan based at least in part on the received modified treatment visualization data to generate a modified treatment plan;
      transmit, at the request of a treating professional, a clinical check file comprising teeth movements for each stage of the modified treatment plan to a consulting professional for review by the consulting professional;
      process the modified treatment plan so as to generate fabrication instructions for fabricating the one or more orthodontic appliances for repositioning the patient's teeth according to the modified treatment plan; and
      transmit the fabrication instructions to the fabrication machine
   wherein the fabrication machine is further configured to receive the fabrication instructions and fabricate the one or more orthodontic appliances according to the modified treatment plan.

2. The system of claim 1, wherein the treatment visualization data comprises one or more of: a right buccal view; a left buccal view; a posterior view; an anterior view; a mandibular occlusal view; a maxillary occlusal view; an overjet view; a left distal molar view; a left lingual view; a lingual incisor view; a right lingual view; a right distal molar view; an upper jaw view; or a lower jaw view.

3. The system of claim 1, wherein the treating professional computer is associated with one or more treating professionals, the one or more treating professionals including dentists or orthodontists.

4. The system of claim 1, further comprising one or more partner computers coupled to the server.

5. The system of claim 4, wherein the one or more partner computers include a financing partner computer.

6. The system of claim 4, wherein the one or more partner computers include a supplier computer.

7. The system of claim 4, wherein the one or more partner computers include a delivery company computer.

8. The system of claim 1, wherein the server performs office management operations in response to input from a treating professional computer.

9. The system of claim 8, wherein the office management operations include one or more of the following: patient scheduling, patient accounting, or claim processing.

10. The system of claim 1, where the server transmits patient information to a second authorized treating professional computer for consultation in response to input from a first treating professional computer.

11. A computer-implemented method for improved generation of digital models for fabricating orthodontic appliances by a fabrication machine, comprising:
   generating treatment visualization data representing an orthodontic treatment plan for teeth of a patient, wherein the treatment visualization data is stored in a file storage subsystem associated with a server, wherein the treatment visualization data is based at least in part on data received from a dental scanner, and wherein the treatment visualization data comprises one or more manipulable 3-D models of the patient's teeth, wherein the one or more manipulable 3-D models are: (1) configured to be displayed in a web browser via a viewer plug-in module as an animated display of the patient's teeth moving through three or more successive arrangements, and (2) configured to allow a user to modify a position of at least one tooth of the one or more manipulable 3-D models by clicking on the at least one tooth in the web browser via the viewer plug-in module using a pointing device;
   transmitting the treatment visualization data to a treating professional computer or a patient computer over the Internet upon an authorized request prior to adjusting of the patient's teeth according to the treatment plan;
   receiving modified treatment visualization data, wherein the modified treatment visualization data comprises a modified tooth position of at least one tooth of the one or more manipulable 3-D models made in the web browser via the viewer plug-in module by a user clicking on the at least one tooth using a pointing device;
   modifying the orthodontic treatment plan based at least in part on the received modified treatment visualization data to generate a modified treatment plan;
   transmitting, at the request of a treating professional, a clinical check file comprising teeth movements for each stage of the modified treatment plan to a consulting professional for review by the consulting professional;
   processing the modified treatment plan so as to generate fabrication instructions for fabricating one or more orthodontic appliances for repositioning the patient's teeth according to the modified treatment plan; and transmitting the fabrication instructions to the fabrication machine, wherein the fabrication machine is configured to receive the fabrication instructions and is configured to fabricate the one or more orthodontic appliances for repositioning the patient's teeth according to the modified treatment plan.

12. The method of claim 11, further comprising providing financing options for the patient using one or more financing partner computers.

13. The method of claim 11, further comprising offering an on-line shop geared to the patient's dental requirements.

14. The method of claim 11, further comprising providing office management utilities for a treating professional.

15. The method of claim 14, wherein the office management utilities include one or more of the following: patient scheduling, patient accounting, or claim processing.

16. The method of claim 11, wherein the viewer plug-in module is configured to allow a treating professional to manipulate one or more manipulable 3-D models of the patient's teeth using the web browser by displaying a plurality of dental views.

17. The method of claim 16, wherein the treatment visualization data includes one or more of the following: a right buccal view; a left buccal view; a posterior view; an anterior view; a mandibular occlusal view; a maxillary occlusal view; an overjet view; a left distal molar view; a left lingual view; a lingual incisor view; a right lingual view; a right distal molar view; an upper jaw view; or a lower jaw view.

18. The method of claim 11, wherein the viewer plug-in module is configured to display x, y and z axes to allow the user to modify the position of the at least one tooth.

19. The method of claim 11, further comprising providing supplemental services to the patient, including teeth whitening services.

20. A computer-implemented method for improved generation of digital models for fabricating orthodontic appliances by a fabrication machine, comprising:

generating treatment visualization data representing an orthodontic treatment plan for a patient's teeth, wherein the treatment visualization data is stored in a file storage subsystem associated with a server, wherein the treatment visualization data is based at least in part on data received from a dental scanner, and wherein the treatment visualization data comprises one or more manipulable 3-D models of the patient's teeth, wherein the one or more manipulable 3-D models are: (1) configured to be displayed in a web browser via a viewer plug-in module as an animated display of the patient's teeth moving through three or more successive arrangements, and (2) configured to allow a user to modify a position of at least one tooth of the one or more manipulable 3-D models by clicking on the at least one tooth in the web browser via the viewer plug-in module using a pointing device;

transmitting the treatment visualization data from a dental server to a treating professional computer over a network upon request prior to adjustment of the patient's teeth according to the treatment plan;

receiving modified treatment visualization data, wherein the modified treatment visualization data comprises a modified tooth position of at least one tooth of the one or more manipulable 3-D models made in the web browser via the viewer plug-in module by a user clicking on the at least one tooth using a pointing device;

modifying the orthodontic treatment plan based at least in part on the received modified treatment visualization data to generate a modified treatment plan;

transmitting, at the request of a treating professional, a clinical check file comprising teeth movements for each stage of the modified treatment plan to a consulting professional for review by the consulting professional;

processing the modified treatment plan so as to generate fabrication instructions for fabricating one or more orthodontic appliances for repositioning the patient's teeth according to the modified treatment plan, wherein the fabrication instructions, when executed by a fabrication machine, cause the fabrication machine to perform a fabrication method, the fabrication method comprising fabricating the one or more orthodontic appliances for repositioning the patient's teeth according to the modified treatment plan; and transmitting the fabrication instructions to the fabrication machine, wherein the fabrication machine is configured to fabricate the one or more orthodontic appliances.

\* \* \* \* \*